US008375961B2

(12) United States Patent
Prokopchuk et al.

(10) Patent No.: US 8,375,961 B2
(45) Date of Patent: Feb. 19, 2013

(54) FLOSS PICK

(76) Inventors: Walter Prokopchuk, King (CA);
Robert G. Dickie, King (CA)

( * ) Notice: Subject to any disclaimer, the term of this patent is extended or adjusted under 35 U.S.C. 154(b) by 0 days.

(21) Appl. No.: 12/939,618

(22) Filed: Nov. 4, 2010

(65) Prior Publication Data

US 2012/0111358 A1  May 10, 2012

(51) Int. Cl.
*A61C 15/00* (2006.01)
(52) U.S. Cl. .................... 132/323; 132/329; 132/321
(58) Field of Classification Search ........... 132/321–329
See application file for complete search history.

(56) References Cited

U.S. PATENT DOCUMENTS

| 542,782 | A | * | 7/1895 | Simons | 132/323 |
|---|---|---|---|---|---|
| 3,106,216 | A | * | 10/1963 | Kirby | 132/326 |
| 3,368,553 | A | | 2/1968 | Kirby | |
| 4,194,290 | A | * | 3/1980 | Vallhonrat | 433/141 |
| 5,184,631 | A | * | 2/1993 | Ikeda | 132/323 |
| 5,692,531 | A | | 12/1997 | Chodorow | |
| 5,704,379 | A | * | 1/1998 | Krynicki | 132/323 |
| 5,737,803 | A | * | 4/1998 | Tisdale | 16/430 |
| 5,806,540 | A | * | 9/1998 | Lee | 132/329 |
| 5,816,271 | A | * | 10/1998 | Urso | 132/322 |
| 5,829,458 | A | | 11/1998 | Chodorow | |
| 6,474,347 | B1 | * | 11/2002 | Hallinder et al. | 132/325 |
| 8,069,865 | B1 | * | 12/2011 | Winter | 132/323 |
| 2003/0111089 | A1 | * | 6/2003 | Gilbert et al. | 132/150 |
| 2011/0186074 | A1 | * | 8/2011 | Misner et al. | 132/323 |

FOREIGN PATENT DOCUMENTS

| CA | 2353885 | 6/2000 |
|---|---|---|
| CN | 201558187 | 8/2010 |

* cited by examiner

*Primary Examiner* — Robyn Doan
(74) *Attorney, Agent, or Firm* — Sand & Sebolt

(57) ABSTRACT

A floss pick including a body with a handle and a head. The head has first and second arms defining a cavity between them, and a length of dental floss extending between the arms and across the cavity. Preferably, the handle is oval in shape for easier grasping by the user. The body includes a toothpick member that preferably is disposed on the head and extends outwardly from one of the first and second arms into the cavity. The floss extends between the other of the first and second arms and the toothpick member and during use guides the toothpick member into interproximal spaces between teeth. Alternatively, a toothpick member may be provided in a recessed region of the handle and extend forwardly toward the head. The latter toothpick member is able to be detached from the handle for separate use.

23 Claims, 25 Drawing Sheets

FLOSS PICK

BACKGROUND OF THE INVENTION

1. Technical Field

This invention generally relates to oral hygiene. More particularly, the invention relates to floss picks. Specifically, the invention relates to a single use, disposable floss pick that incorporates a shielded toothpick member or dental stimulator, with the toothpick member preferably being provided on the head of the floss pick and disposed at the end of a tensioned length of dental floss.

2. Background Information

Floss picks are small, plastic, Y-shaped or F-shaped oral care devices that comprise a molded plastic frame into which a short length of floss thread is secured. These handy, single-use devices are sold in packs of 50 or more and are much easier to use than a traditional spooled floss that needs to be wrapped around one's fingers.

Floss picks can have a wide variety of handle styles that typically are shaped to end in a sharp point. The pointed ends are designed to be used as a toothpick. The combination of the floss and the toothpick aid the user in maintaining good oral habits. An example of a previously known toothpick is found in U.S. Pat. No. 5,692,531 (Chodorow) which discloses a floss pick that includes portions of the handle shaped to terminate in a sharp end which can then be used as a toothpick.

Presently known floss picks do, however, have a problem in that, if the user is not careful, they can prick the inside of their hands and fingers while they are using the floss end of the device. Some manufacturers have attempted to address this issue. For example, U.S. Pat. No. 5,829,458 (Chodorow) discloses a floss pick comprising a body made up of a head and a handle. The head includes two arms between which a length of floss is strung. The handle extends outwardly from the head. A toothpick is formed as part of the handle. The toothpick is not formed at the end of the handle remote from the head but is instead preferably formed along an edge of the handle. The handle also includes another portion that acts as a guard for the toothpick and prevents the user from being accidentally pricked by the toothpick. The user simply bends the guard out of the way when they wish to use the floss pick and bends it back into the way when they want to shield the pick. The problem with this device is that if the user decides to use the toothpick end of the device first, then the bent back guard is unable to maintain its position during the flossing operation after it has been moved back to the guard position. The user can then, once again, accidentally injure themselves on the toothpick because of the bent guard. Alternatively, instead of the guard being bent out of the way it may be completely removed from the floss pick to reveal the toothpick portion.

A second issue that has been evident with prior known devices is that the toothpick point itself is not thin enough to function in the same manner as a wooden toothpick would be able to do. The reason for this is fairly simple. The body of the floss pick is made from ABS or styrene plastic that has to be made so that it is approximately 0.08 inches thick. This thickness is necessary because the body will deform during use if the plastic is any thinner. The 0.08 inch thickness is usually tapered in two dimensions to form the sharpened end of the toothpick point. The points are similar to traditional wooden toothpicks. The ABS or styrene plastic is very much harder than wood and thus is more difficult to deform or crush to a sufficient degree to allow the point of the toothpick to enter narrower interproximal spaces between teeth.

There is therefore a need for an improved floss pick that addresses the safety issue of the sharpened point at the end of the floss pick handle and which includes a toothpick that is better able to reach into narrower interproximal spaces.

SUMMARY OF THE INVENTION

The device of the present invention comprises a floss pick which includes a body with a handle and a head. The head has first and second arms defining a cavity between them, and a length of dental floss that extends between the arms and across the cavity. The body includes a toothpick member that preferably is disposed on the head and extends outwardly from one of the first and second arms into the cavity. The floss extends between the other of the first and second arms and the toothpick member and during use guides the toothpick member into interproximal spaces between teeth.

The toothpick member includes one or more blades and is tapered from adjacent the one of the first and second arms to an end remote therefrom. The one or more blades may be sinuous along their length or may be planar. A combination of sinuous and planar blades may also be utilized. In addition, an elastomeric sheath may be provided around an exterior surface of the blades so that the toothpick member may be utilized as a dental stimulator.

The handle preferably is oval in shape or includes an oval recess therein. The oval shaped handle or recess is configured to be grasped between a user's thumb and index finger.

As an alternative to the toothpick member on the head of the floss pick, the device may, instead, be provided with a detachable toothpick member on the handle. Preferably, this toothpick member extends forwardly toward the head of the floss pick and is initially coplanar with the front and rear surfaces of the handle so that it will not accidentally injure the user. Furthermore, the apex of the toothpick is preferably slightly rounded so that it additionally cannot accidentally hurt the user.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Figure 12:
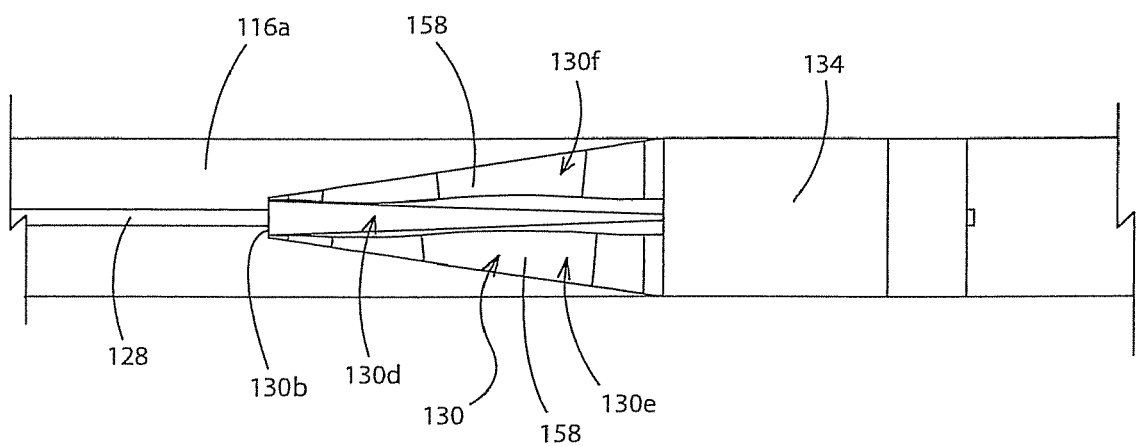
FIG. 12 is a bottom view of FIG. 10.
Figure 13:
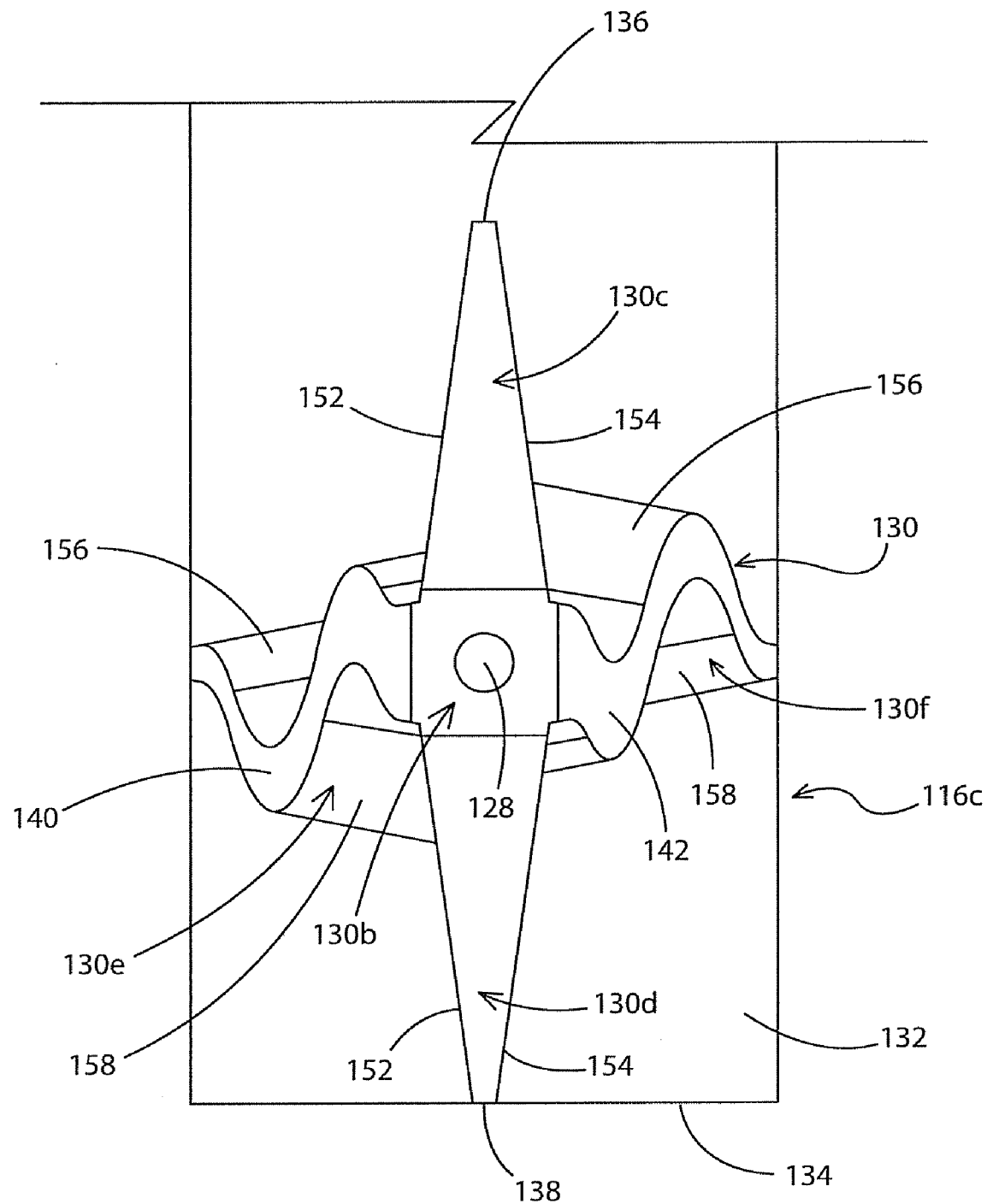
FIG. 13 is a side view of FIG. 10.
Figure 14:
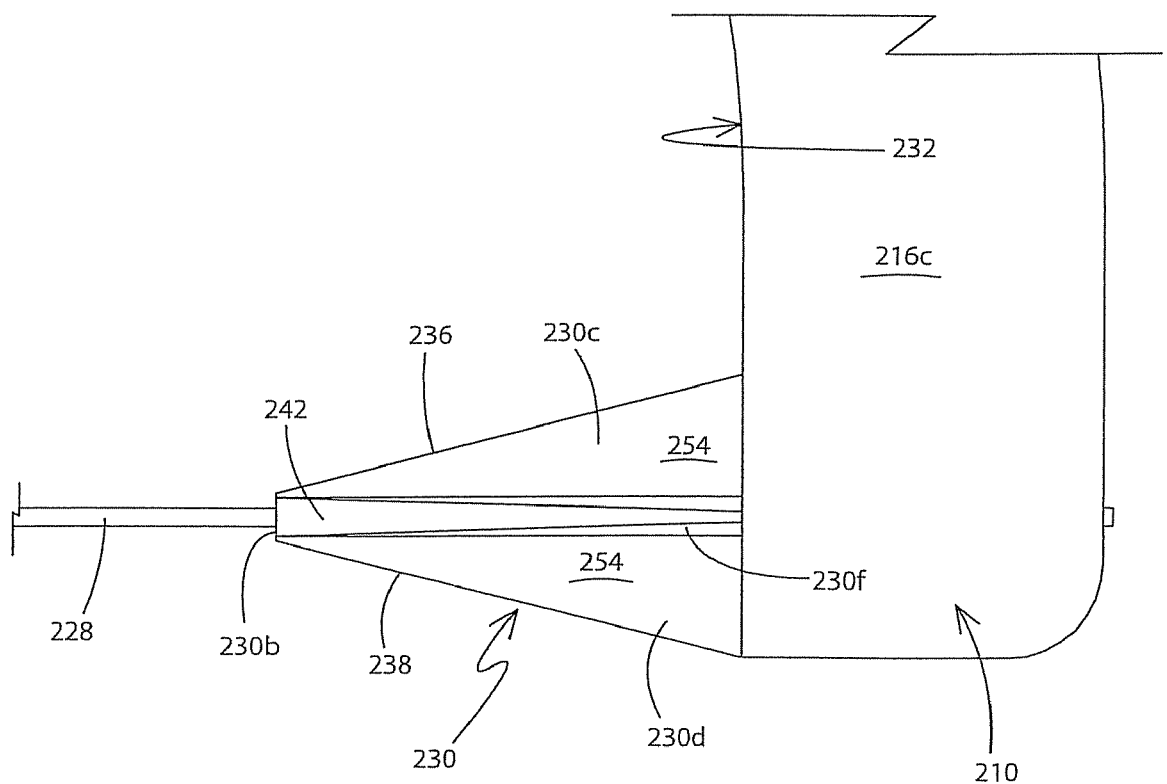
FIG. 14 is an enlarged front view of a third embodiment of a toothpick region of a floss pick of the present invention.

Referring to FIGS. 1-6, there is shown a first embodiment of a floss pick in accordance with the present invention and indicated generally at 10. FIGS. 7-12 show a second embodiment of a floss pick in accordance with the present invention indicated generally at 110. FIGS. 13 and 14 show a third embodiment of a toothpick region of a floss pick in accordance with the present invention, where the floss pick is indicated by the reference character 210. FIGS. 15-19 show a fourth embodiment of a floss pick in accordance with the present invention indicated generally by the reference character 310. Finally, FIGS. 20-23b show a fifth embodiment of a floss pick in accordance with the present invention and indicated by the reference character 410.

Floss picks 10, 110, 210, 310, and 410 preferably are single use, disposable picks that are injection molded from a suitable material such as Acrylonitrile Butadiene Styrene (ABS) plastic.

Figure 1:
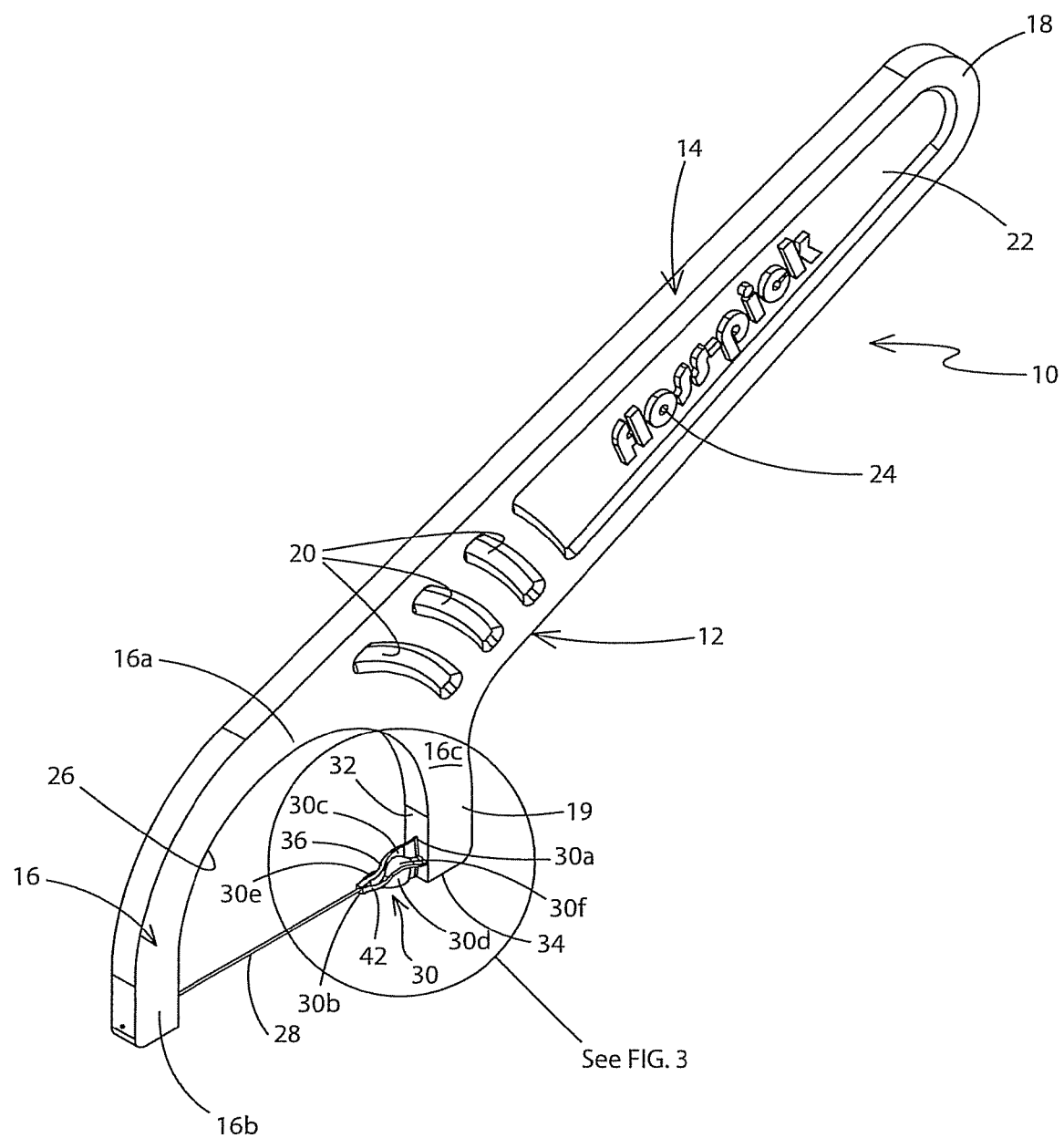
FIG. 1 is a perspective front view of a first embodiment of a floss pick in accordance with the present invention.
Figure 2:
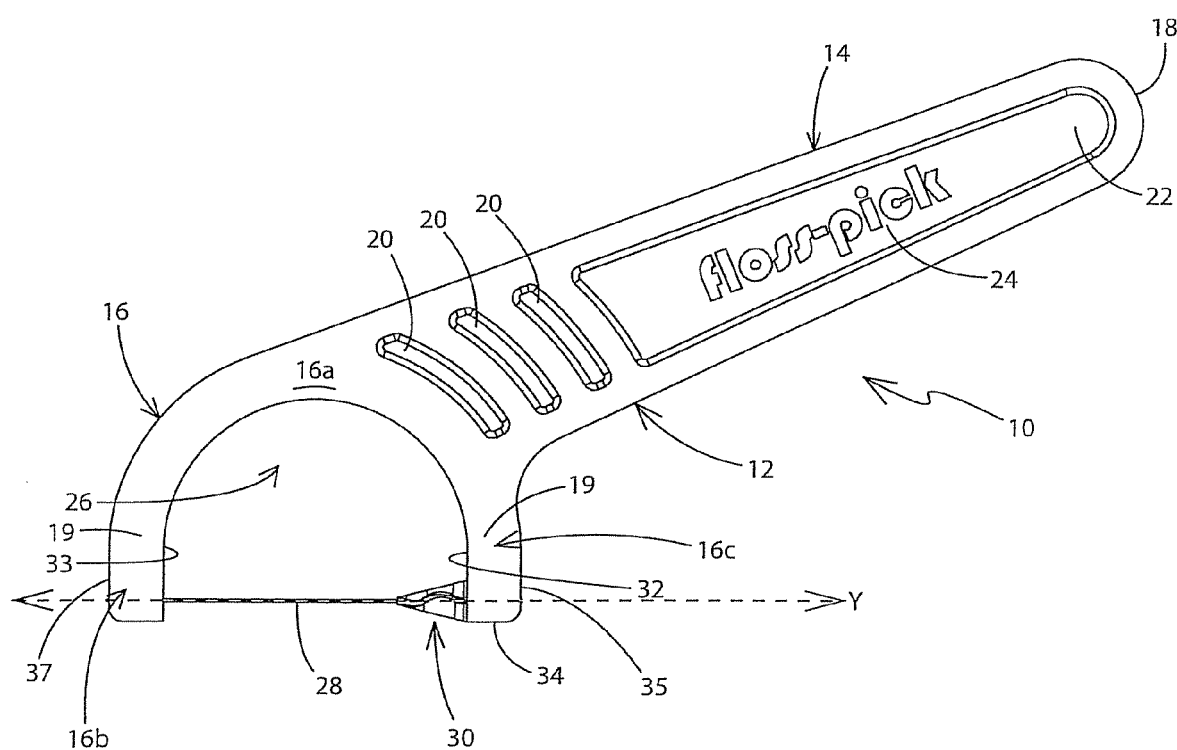
FIG. 2 is a front view thereof.

Referring to FIGS. 1-7b, floss pick 10 comprises a body 12 including a handle 14 and a head 16. FIG. 2 shows a front view of floss pick 10 and it should be understood that, although not illustrated herein, a rear view of floss pick 10 is substantially a mirror image of FIG. 2. Thus, body 12 has a front surface 12a (FIG. 2) and a rear surface 12b (FIG. 5) that are mirror images of each other. Head 16 preferably is disposed at an angle relative to handle 14 and body 12 is generally F-shaped. It will be understood, however, that body 12 of pick 10 may, alternatively, be generally Y-shaped or of any other suitable shape without departing from the scope of the present invention.

Handle 14 extends outwardly from an end of head 16 and tapers to a terminal end 18. In accordance with a specific feature of the invention, terminal end 18 preferably is gently rounded so that when pick 10 is held by a user, the terminal end 18 will not cause injury to the user's hand. Handle 14 preferably defines one or more cavities 20 that serve to reduce the amount of material required to produce pick 10. Pick 10 may also include a recessed region 22 defined in each of the front surface 12a and rear surface 12b of handle 14 of body 12. Only one of said recessed regions 22 is illustrated in the attached figures. Recessed regions 22 aid in reducing the amount of material required to produce pick 10. Recessed regions 22 also provide an area on each side of handle 14 upon which indicia 24 may be applied. Suitable indicia 24 include a brand name or instructions for use of pick 10. Indicia 24 preferably are molded or printed onto an interior wall of recessed region 22.

Head 16 preferably is generally U-shaped and includes a central region 16a, a first arm 16b and a second arm 16c. Central region 16a, and first and second arms 16b, 16c define a C-shaped cavity 26. Each of central region 16a, first arm 16b and second arm 16c has a front surface 19 (FIG. 6), a rear surface 21, and an interior surface and an exterior surface which extend between the front and rear surfaces 19, 21. The interior and exterior surfaces of first arm 16b are indicated at 33 and 35, respectively (FIG. 2), and the interior and exterior surfaces of second arm 16c are indicated at 32 and 37, respectively.

At least one length of floss 28 extends between first and second arms 16b, 16c and more specifically, between interior surfaces 33 and 32 thereof. Floss 28 extends across cavity 26 and may be disposed at any one of a number of angles relative to interior surfaces 32, 33. However, Floss 28 preferably is secured generally at right angles to interior surfaces 32, 33. Floss 28 preferably is fixedly secured in place so that it is retained under tension. It will be understood that head 16 may take other configurations that permit one or more strands of floss 28 to extend across an open region so that the floss is positioned to readily be engaged in the interproximal space 46 (FIGS. 7a, 7b) between the surfaces of two adjoining teeth (48, 50).

In accordance with a specific feature of the present invention, a toothpick member 30 is disposed on body 12. Toothpick member 30 specifically is provided on head 16. More specifically, toothpick member 30 is provided on one of first and second arms 16b, 16c and preferably is disposed on the one of the arms that is closer to the terminal end 18 of handle 14. In FIGS. 1-6, toothpick member 30 preferably is disposed on second arm 16c as this is the region of floss pick 10 that will engage the surface of the teeth when the user applies a pushing force on the pick 10 as opposed to a pulling force.

Figure 6:
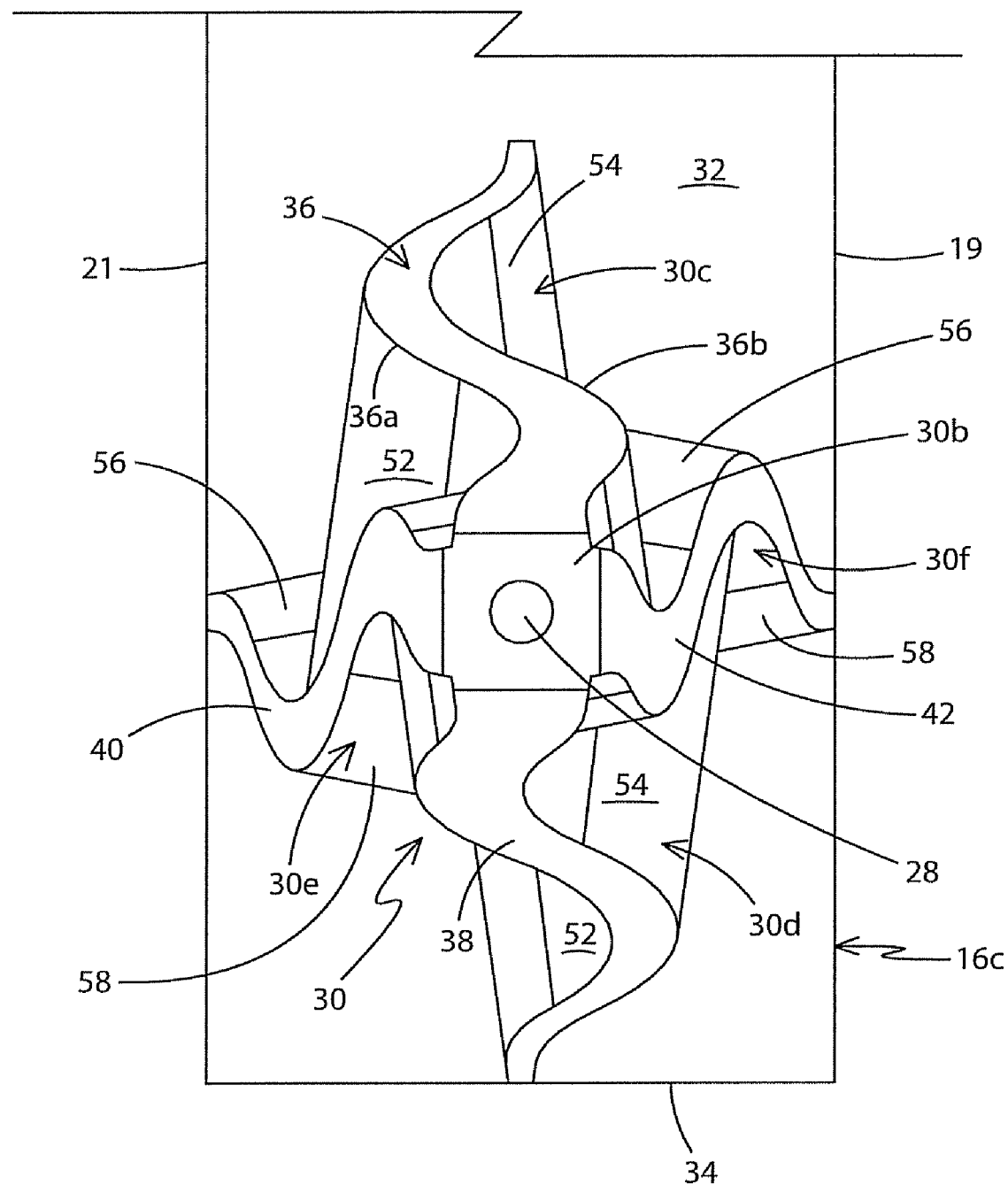
FIG. 6 is a side view of FIG. 3.

In accordance with yet another specific feature of the present invention, toothpick member 30 extends outwardly from interior surface 32 of second arm 16c and into cavity 26 and toward interior surface 33 of first arm 16a. FIG. 2 shows that floss 28 has an axis "Y" and toothpick member 30 has a longitudinal axis that is parallel to or aligned with the axis "Y" of floss 28. As shown in FIG. 6, preferably no portion of toothpick member 30 extends outwardly beyond one or both of the front and rear surfaces 19, 21 of second arm 16c. Still further, preferably no portion of toothpick member 30 extends beyond the outermost end 34 of second arm 16c. Toothpick member 30 is thus shielded from accidental contact by the user's hand during use of floss pick 10. It will be understood that it is possible for a portion of toothpick member 30 to extend slightly beyond one or more of front surface 19, rear surface 21 and outermost end 34 of second arm 16c but a second end 30b of toothpick member 30 preferably is always located inwardly of these surfaces so that a user will not accidentally come into contact with second end 30b.

Figure 3:
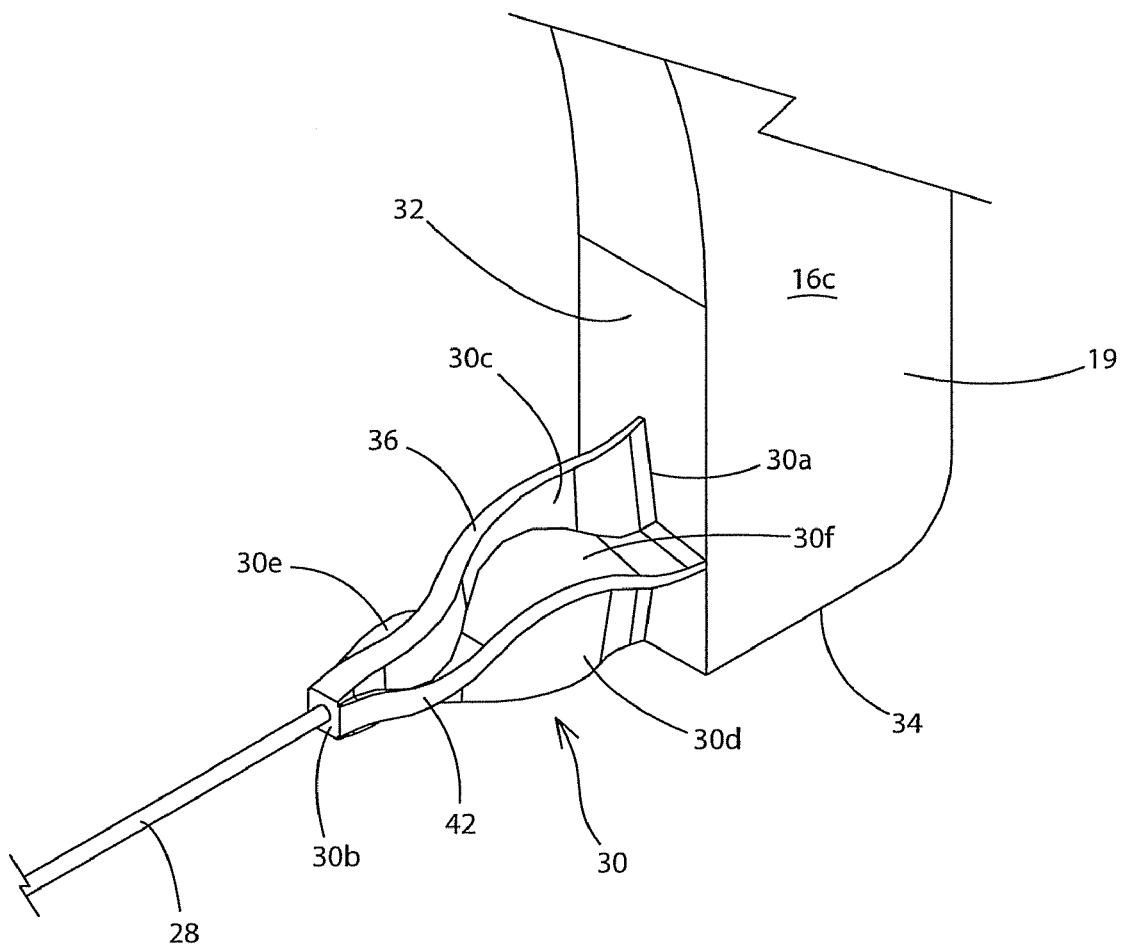
FIG. 3 is an enlarged perspective view of the highlighted region of FIG. 1.
Figure 4:
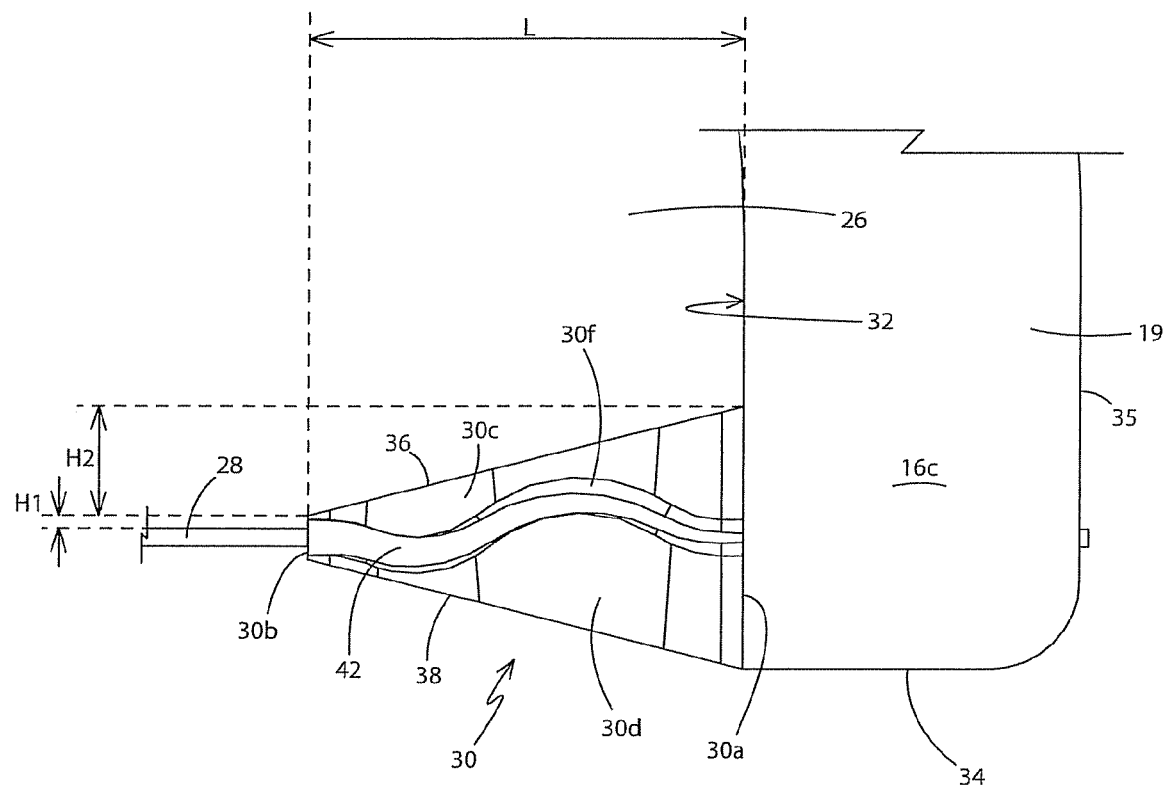
FIG. 4 is a front view of FIG. 3.
Figure 5:
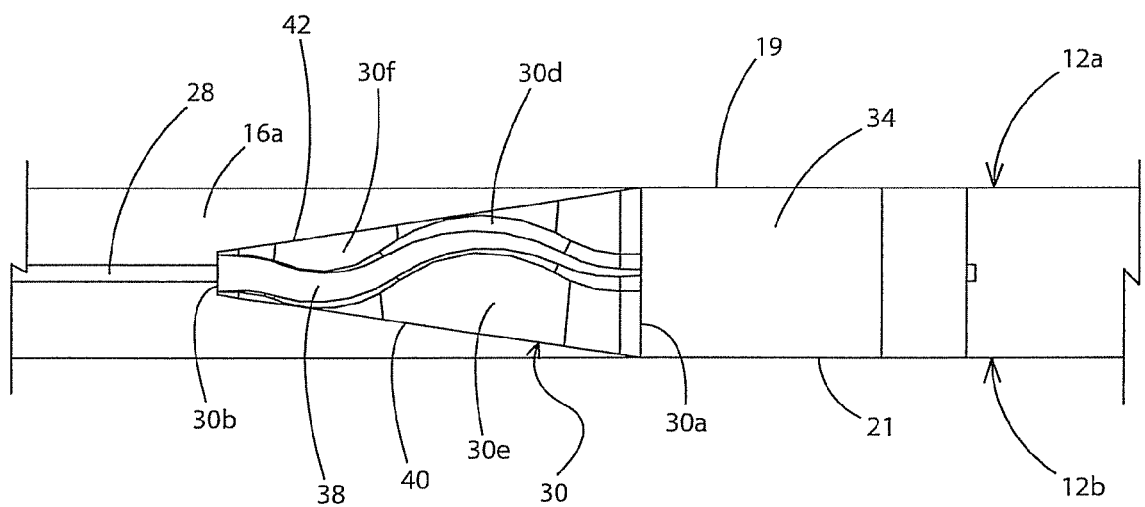
FIG. 5 is a bottom view of FIG. 3.

In accordance with yet another specific feature of the present invention and referring to FIGS. 3 and 4, toothpick member 30 is generally arrowhead-shaped and extends outwardly from interior surface 32 of second arm 16c. Toothpick member 30 has a first end 30a (FIG. 4) adjacent interior surface 32 and a second end 30b disposed a spaced distance from interior surface 32. Preferably, toothpick member 30 tapers from first end 30a to second end 30b thereof. Toothpick member 30 may comprise a separate component that is secured to interior surface 32 or it may be integrally formed therewith. The longitudinal axis of toothpick member 30 extends between first and second ends 30a, 30b and preferably is substantially at right angles to interior surface 32. Second end 30b may be flattened and generally parallel to interior surface 32.

At least one blade is provided on toothpick member 30 extending radially outwardly from the longitudinal axis thereof. Preferably, four blades are provided on toothpick member 30, namely first blade 30c, second blade 30d, third blade 30e and fourth blade 30f. Each blade 30c-30f extends radially outwardly away from the longitudinal axis of toothpick member 30 and generally at right angles thereto. Furthermore, each blade 30c-30f extends rearwardly from second end 30b of toothpick member 30 and terminates at first end 30a thereof. First and second blades 30c, 30d are generally vertically oriented and third and fourth blades 30e, 30f are generally horizontally oriented. Consequently, each blade is disposed generally at ninety degrees relative to the adjacent blades and blades 30c-30f intersect each other along their bases (unnumbered). It will be understood that toothpick member 30 may include more than four blades or less than four blades without departing from the scope of the invention and that these blades may be disposed at angles other than ninety degrees relative to each other.

Each blade 30c-30f has a first side wall and a second side wall that are opposed to each other and extend from first end 30a to second end 30b of toothpick member 30. The first side wall and second side wall are numbered 52 and 54, respectively, for each of first and second blades 30c, 30d. First side wall and second side wall are numbered 56 and 58, respectively, for third and fourth blades 30e, 30f. First blade 30c extends upwardly and outwardly away from first sides walls 56 of third and fourth blades 30e, 30f. Second blade 30d extends downwardly and outwardly away from second side walls 58 of third and fourth blades 30e, 30f. Third blade 30e extends horizontally outwardly away from a first side wall 52 of each of the first and second blades 30c, 30d. Fourth blade 30f extends horizontally outwardly away from a second side wall 54 of each of the first and second blades 30c, 30d.

Each blade 30c-30f further includes a base (unnumbered) disposed proximate or in abutting contact with the two adjacent blades and has an outermost wall remote therefrom. The base and outermost wall extend between the first and second side walls thereof and extend between first end 30a and second end 30b of toothpick member 30. The outermost walls of blades 30c-30f are numbered 36, 38, 40 and 42 respectively. Each of the outermost walls 36-42 is disposed generally at right angles relative to the two adjacent outermost walls.

First and second blades 30c, 30d are disposed substantially at 180 degrees relative to each other, are substantially identical in shape and are mirror images of each other. Similarly, third and fourth blade 30e, 30f are disposed substantially at 180 degrees to each other, are substantially identical in shape and are mirror images of each other.

As can best be seen in FIG. 6, toothpick member 30 has a generally undulating X-shape when viewed from second end 30b and toward interior surface 32. In accordance with another specific feature of the present invention, all four of the blades 30c-30f are sinuous along their lengths "L" (FIG. 4) as measured between second end 30b and interior surface 32. Each of first, second, third and fourth blades 30c-30f taper in height along their lengths from interior surface 32 to second end 30b. Consequently, each of first, second, third and fourth blades 30c-30f are of the shortest height "H1" (FIG. 4) adjacent second end 30b and of the greatest height "H2" adjacent interior surface 32. Only the heights H1 and H2 of first blade 30c are shown on FIG. 4 for the sake of clarity but it will be understood that second, third, and fourth blades 30d, 30e and 30f are similarly shaped.

The width of first blade 30c as measured from first side wall 52 to second side wall 54 thereof preferably remains substantially constant for substantially the entire length of first blade 30c. This is true for each of second, third and fourth blades 30d-30f as well. Each of the outermost walls 36-42 of blades 30c-30f are generally flattened along their lengths. Each of the outermost walls 36-42 has longitudinal edges that extend from second end 30b to interior surface 32. For the sake of clarity, only the edges of outermost wall 36 of first blade 30c are numbered on FIG. 6 as edges 36a and 36b. The width of the outermost walls 36, 38, 40, and 42 as measured between the edges 36a, 36b, for example, preferably taper from adjacent second end 30b to adjacent interior surface 32. Preferably, outermost wall 38 of second blade 30d is substantially continuous with outermost end 34 of second arm 16c.

The heights and widths of the four blades and the widths of the outermost walls may all be substantially identical or the first and second blades 30c, 30d may be substantially equal to each other and the third and fourth blades 30e, 30f may be substantially equal to each other but different from the first and second blades. The taper on the first, second, third and fourth blades permits the blades to deform more easily and thereby allows toothpick member 30 to more deeply penetrate into an interproximal space 46 (FIG. 7a) as will be hereinafter described.

As indicated previously, floss 28 extends between first arm 16b and second arm 16c. Specifically, floss 28 extends between the interior surface 33 (FIG. 2) of first arm 16b and second end 30b of toothpick member 30. Floss 28 may be integrally formed with first arm 16b and toothpick member 30 or it may be secured in some suitable manner to each of first arm 16b and toothpick member 30. The longitudinal axis of toothpick member 30 is aligned with the longitudinal axis "Y" of floss 28.

It will further be understood that the toothpick member may be located on interior surface 33 of first arm 16b instead of on second arm 16c. Additionally, a toothpick member may be located on the interior surfaces 33, 32 of each of the first and second arms 16b, 16c and the length of floss 28 extend between the second ends of the two opposed toothpick members.

Figure 7A:
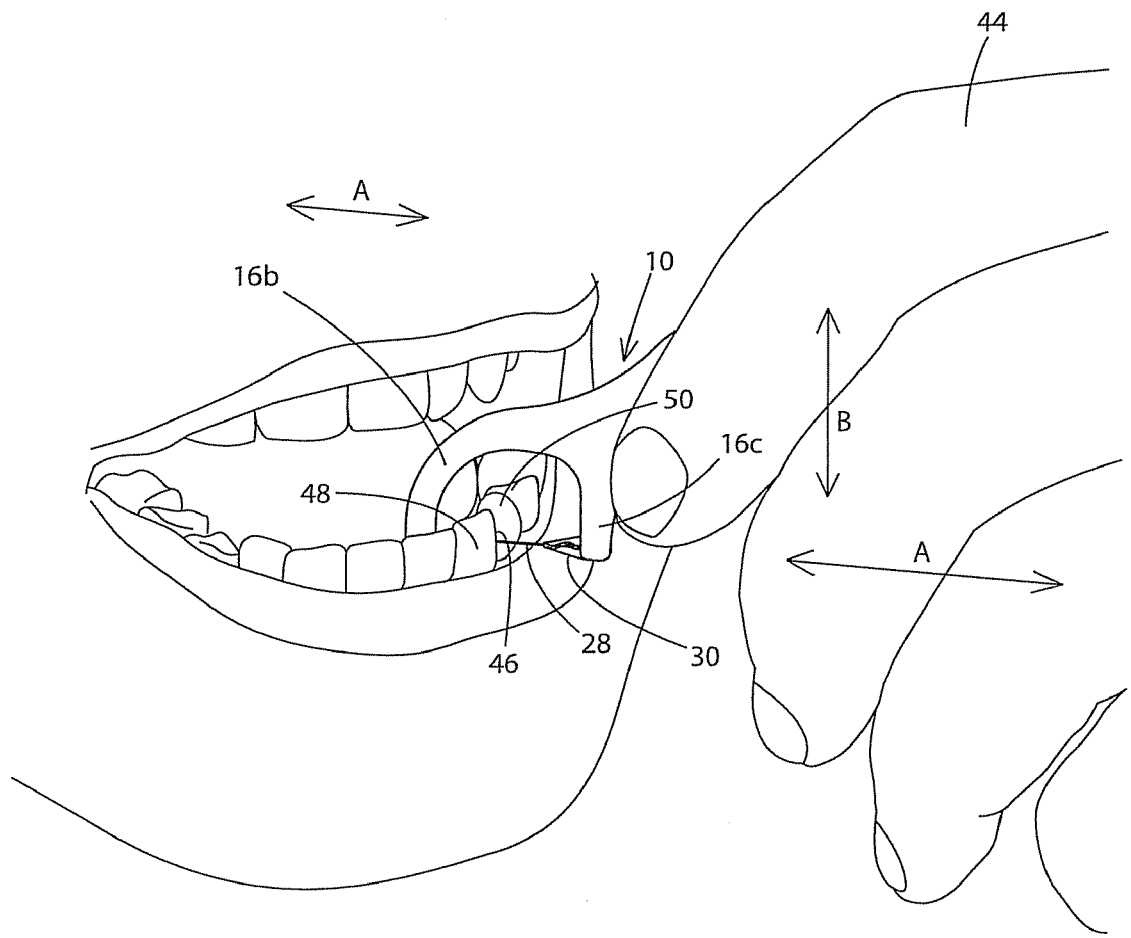
FIG. 7a is a perspective front view showing the floss pick of FIG. 1 being used to floss the user's teeth.
Figure 7B:
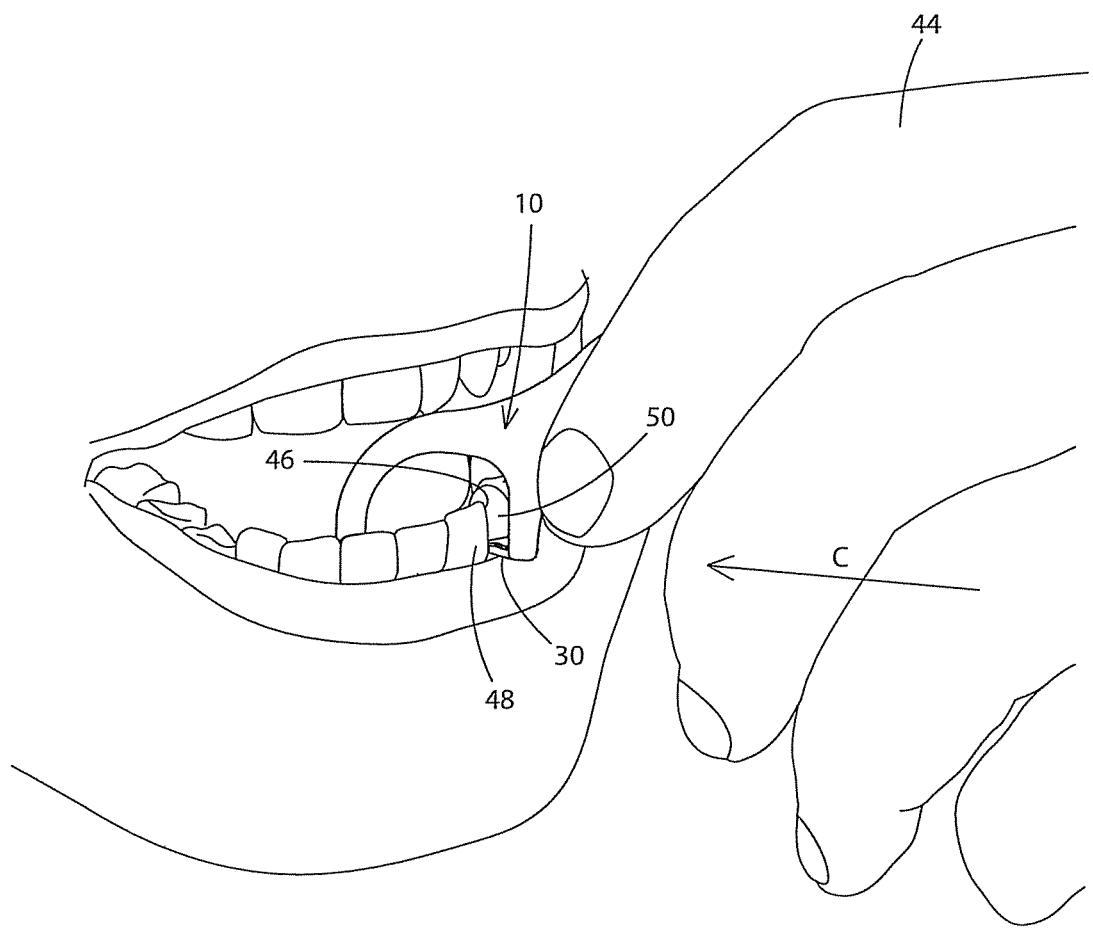
FIG. 7b is a perspective front view showing the toothpick member of the floss pick of FIG. 1 being used to remove debris from an interproximal space.
Figure 8:
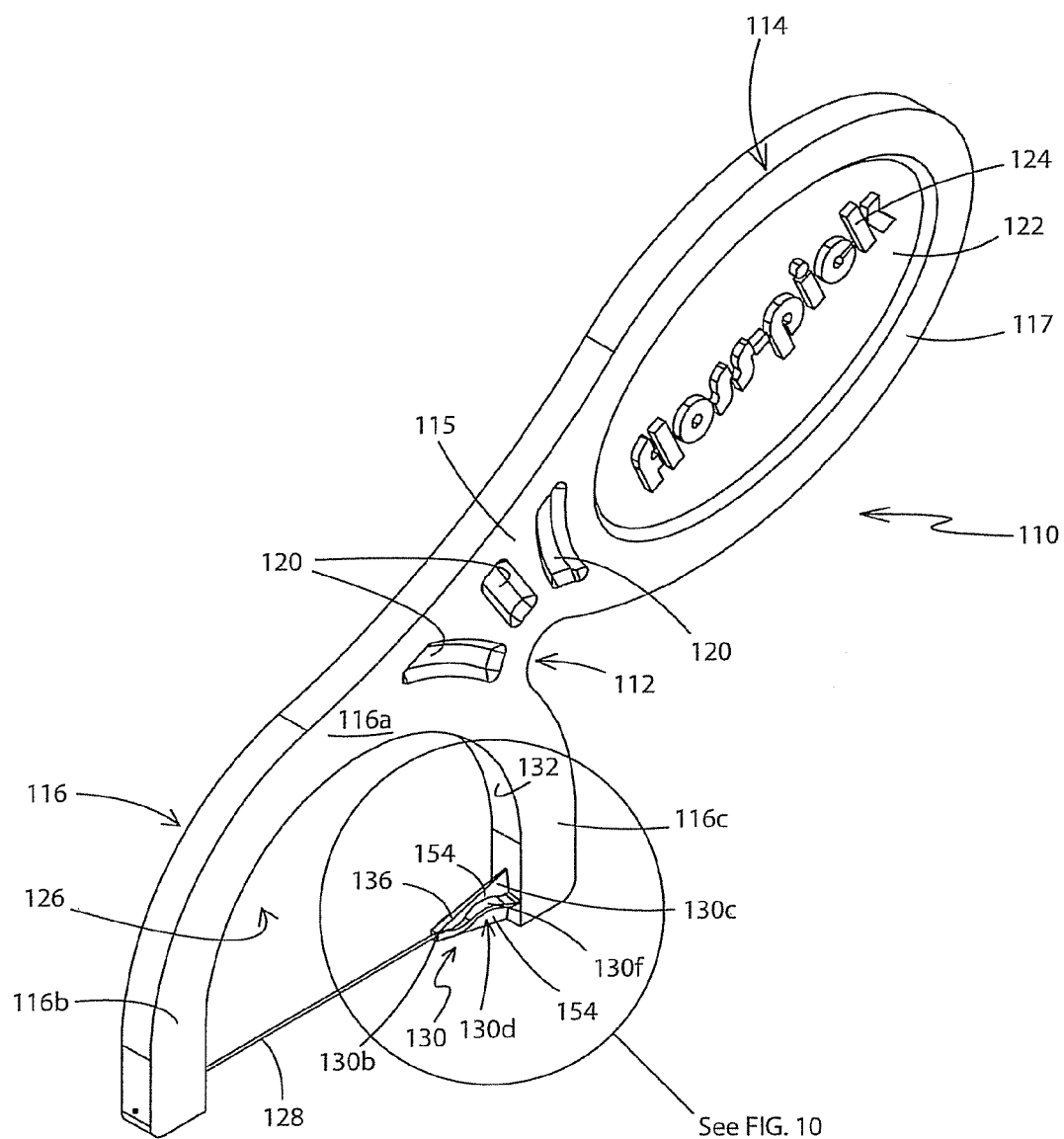
FIG. 8 is a perspective front view of a second embodiment of a floss pick in accordance with the present invention showing an alternative handle design and an alternative toothpick design to those shown in FIG. 1.

Referring to FIGS. 7a and 7b, the device of the present invention is used in the following manner. The user grasps handle 14 of floss pick 10 between the thumb and index finger of their hand 44. They position floss pick 10 so that floss 28 slides into interproximal space 46 between a first tooth 48 and a second tooth 50. In order to floss the teeth 48, 50, floss pick 10 is manipulated by making small movements back-and-forth as indicated by arrow "A", up-and-down as indicated by arrow "B" and side-to-side to remove plaque and debris from portions of the front and rear surfaces of teeth 48, 50.

In order to use toothpick member 30, floss pick 10 is moved in the direction of arrow "C" (FIG. 7b) so that floss 28 guides second end 30b of toothpick member 30 into interproximal space 46 as floss 28 is already positioned therein. Floss pick 10 is then moved up-and-down, side-to-side and in- and out and necessary to remove trapped debris or plaque from the surfaces of teeth 48, 50 from space 46. Once finished, the user moves floss pick upwardly so as to slide floss 28 and/or toothpick member 30 out of interproximal space 46. Floss pick 10 is then moved laterally to engage floss 28 in the next adjacent interproximal space. When the user is finished, floss pick 10 is thrown away.

The overall configuration of toothpick member 30 has been found to result in an effective tool for removing plaque from interproximal spaces between teeth. The combination of the sinuous, tapered and flattened surfaces of toothpick member 30, along with edges, such as 36a and 36b (FIG. 6) of the outermost walls 36-42, all aid in toothpick member 30 being effective to scrub plaque and debris from the teeth.

Figure 9:
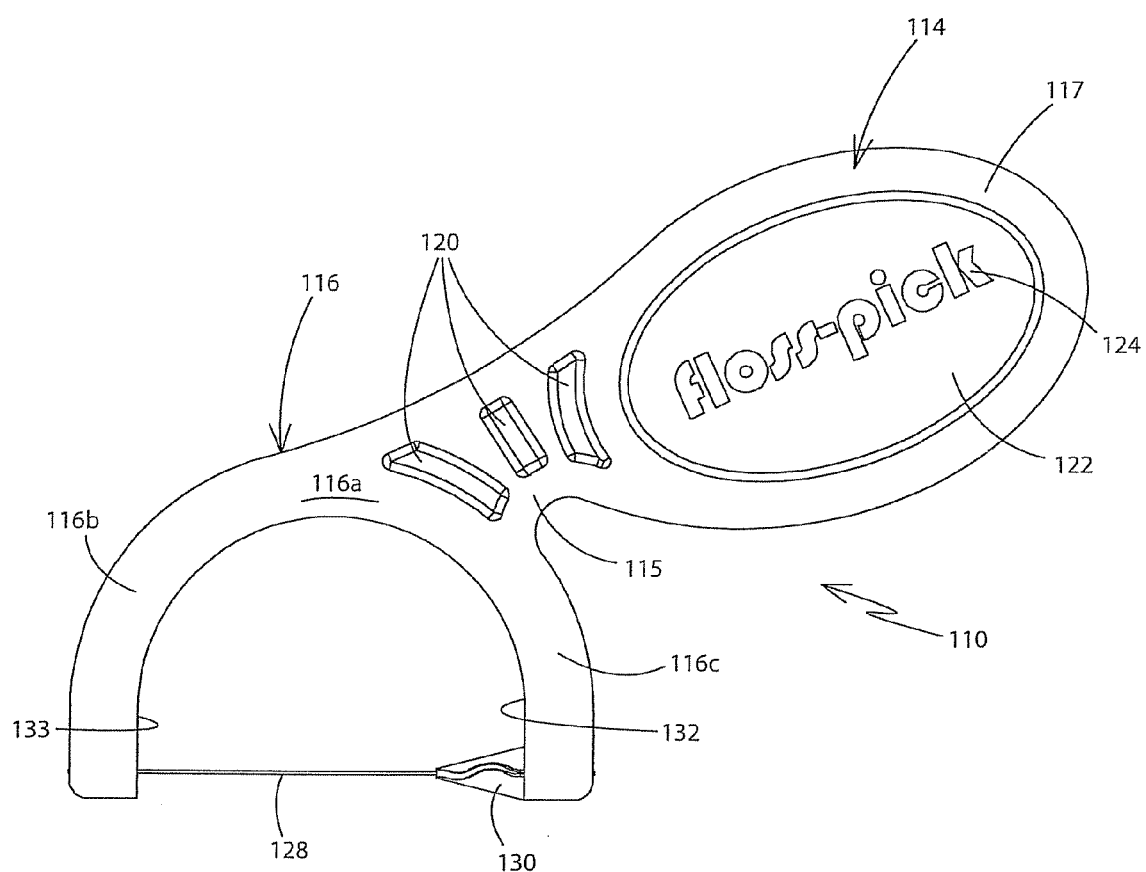
FIG. 9 is a front view thereof.
Figure 10:
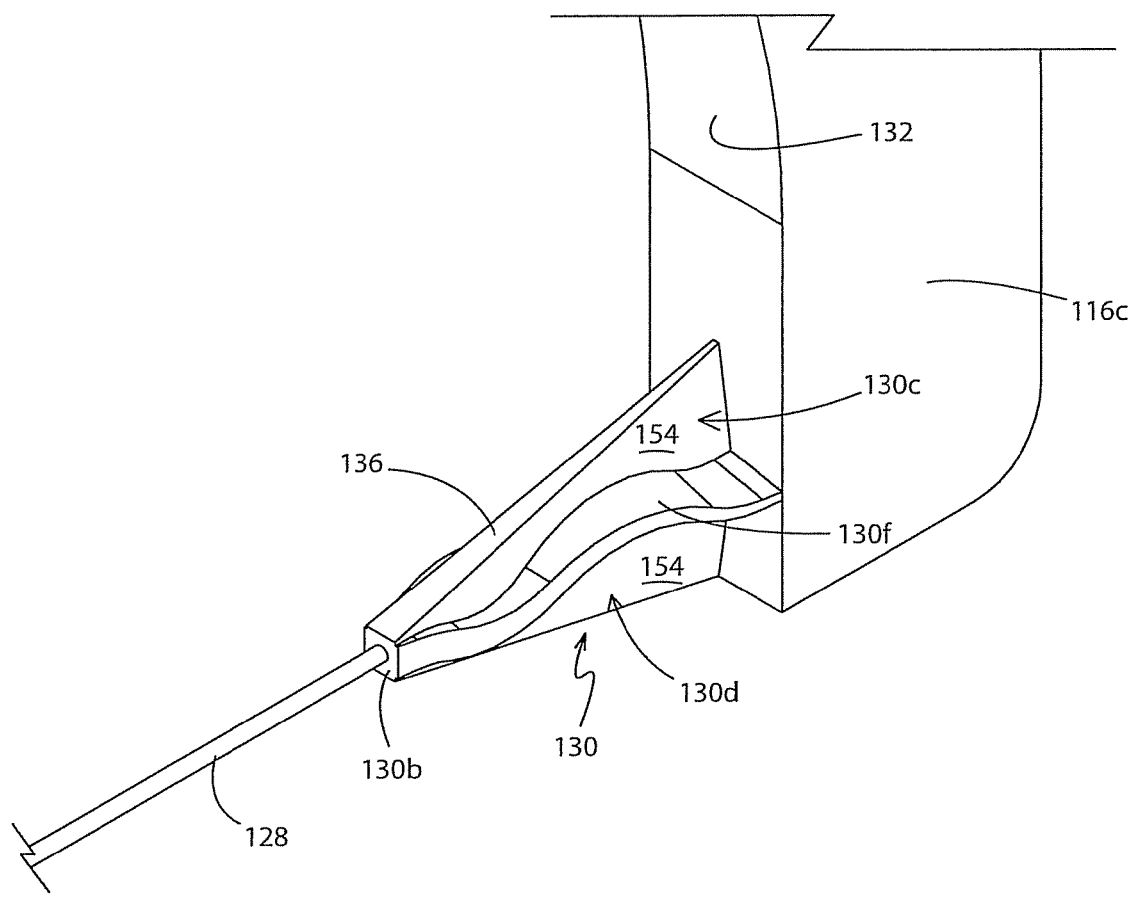
FIG. 10 is an enlarged perspective view of the highlighted region of FIG. 8.
Figure 11:
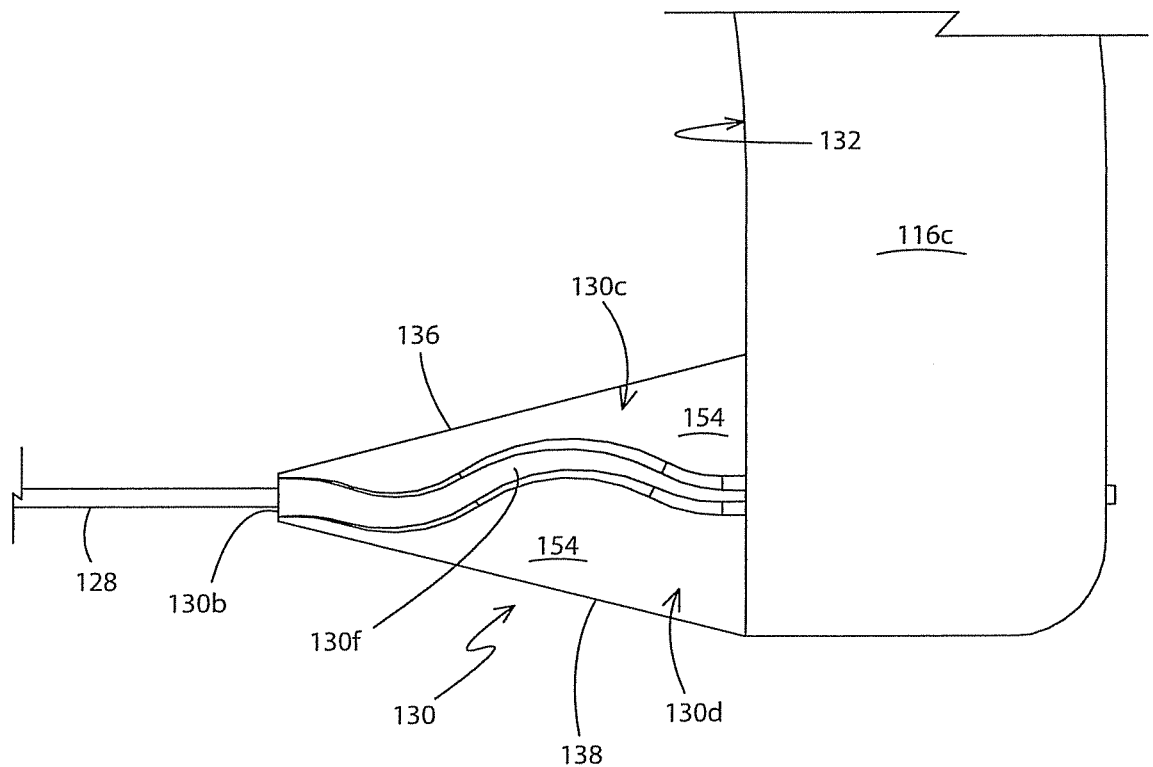
FIG. 11 is a front view of FIG. 10.

Referring to FIGS. 8-13 there is shown a second embodiment of a floss pick in accordance with the present invention indicated generally at 110. Floss pick 110 comprises a body 112 including a handle 114 and a head 116. Head 116 preferably is disposed at an angle relative to handle 114 and body 112 is generally F-shaped. Handle 114 extends outwardly from a rear end of head 116 and includes a neck 115 and a generally oval lobe 117. Neck 115 preferably defines one or more cavities 120. Lobe 117 defines a recessed region 122 on each of the front and rear surfaces of handle 114. Indicia 124 may be applied to the interior wall of recessed region 122. As with the previous embodiment, only the recessed region 122 on the front surface of handle 114 is illustrated in the attached figures but a substantially identical recessed region 122 is provided in the rear surface. Lobe 117 and recessed regions 122 therein preferably are sized so that the pad of a user's thumb is received in one of recessed regions 122 and the pad of the user's index finger is received in the other of the recessed regions 122. In accordance with one of the specific features of the present invention and as shown in FIG. 9, the oval shape of lobe 117 and the width of the handle 114 as measured between the front and rear surfaces thereof, enable the user to more readily and easily grip floss pick 110 than was the case with previously known devices.

As with the first embodiment, head 116 preferably is generally U-shaped and includes a central region 116a, a first arm 116b and a second arm 116c. Central region 116a, and first and second arms 116b, 116c define a C-shaped cavity 126. At least one length of floss 128 extends between first and second arms 116b, 116c. In accordance with a specific feature of the present invention, however, a second embodiment of a toothpick member 130 is disposed on body 112. Toothpick member 130 specifically is provided on head 116, and not on the handle 114 as was the case with previously known floss picks. Toothpick member 130 is provided on one of first and second arms 116b, 116c and preferably is integrally formed with and extends outwardly from an interior surface 132 of second arm 116c and into cavity 126.

Toothpick member 130 is shown in greater detail in FIGS. 10-13. Toothpick member 130 includes a second end 130b spaced a distance away from interior surface 132 of second arm 116c. Preferably, second end 130b is generally parallel to interior surface 132. Four blades extend outwardly and rearwardly from second end 130b and toward interior surface 132, namely, first blade 130c, second blade 130d, third blade 130e and fourth blade 130f. First and second blades 130c, 130d are generally vertically oriented and third and fourth blades 130e, 130f are generally horizontally oriented. First blade 130c extends upwardly and outwardly away from upper surfaces of third and fourth blades 130e, 130f. Second blade 130d extends downwardly and outwardly away from lower surfaces of third and fourth blades 130e, 130f. Third blade 130e extends horizontally outwardly away from a left side wall of each of the first and second blades 130c, 130d. Fourth blade 130f extends horizontally outwardly away from a right side wall of each of the first and second blades 130c, 130d.

In accordance with the present invention and as can best be seen in FIG. 13, toothpick member 130 is generally X-shaped when viewed from second end 130b and toward interior surface 132. First and second blades 130c, 130d are substantially identical to each other and third and fourth blades 130e, 130f are substantially identical to each other. In accordance with a specific feature of the present invention, first and second blades 130c, 130d are generally a truncated-triangle in cross-sectional shape. Each of first and second blades 130c, 130d has generally planar and straight first and second side walls 152, 154 and has generally planar and straight outermost walls 136, 138, respectively. The term "straight" as used herein indicates that the blade or outermost wall is substantially free of curves. Each of first and second blades 130c, 130d taper in width from their bases adjacent the third and fourth blades 130e, 130f to adjacent their outermost walls 136, 138. Additionally, first and second blades 130, 130d taper in height from adjacent interior surface 132 to adjacent second end 130b. Additionally, the width of each outermost wall 136, 138 tapers from adjacent second end 130b to adjacent interior surface 132. This is seen in FIG. 12. Preferably, outermost wall 138 of second blade 130d is substantially continuous with outermost end 134 of second arm 116c.

In accordance with yet another feature of the present invention, third and fourth blades 130e, 130f are sinuous along their lengths between second end 130b and interior surface 132. Each of the third and fourth blades 30e, 30f has a generally flattened outermost wall with the outermost wall of third blade 130e being indicated at 140 and the outermost wall of fourth blade 130f being indicated at 142. Third and fourth blades 130e, 130f are substantially identical to third and fourth blades 30e, 30f and therefore won't be described in any additional detail herein.

It will be understood that instead of first and second blades 30c, 30d walls being generally planar along their lengths and third and fourth blades 30e, 30f being generally sinuous, first and second blades may be sinuous and third and fourth blades may be substantially planar, without departing from the spirit of the present invention.

Floss 128 extends between first arm 116b and second arm 116c. Specifically, floss 128 extends between the interior surface 133 (FIG. 9) of first arm 116b and second end 130b of toothpick member 130. Floss 128 may be integrally formed with first arm 116b and toothpick member 130 or it may be secured in some suitable manner to each of first arm 116b and toothpick member 130. Floss pick 110 is used in substantially the same manner as floss pick 10.

Figure 15:
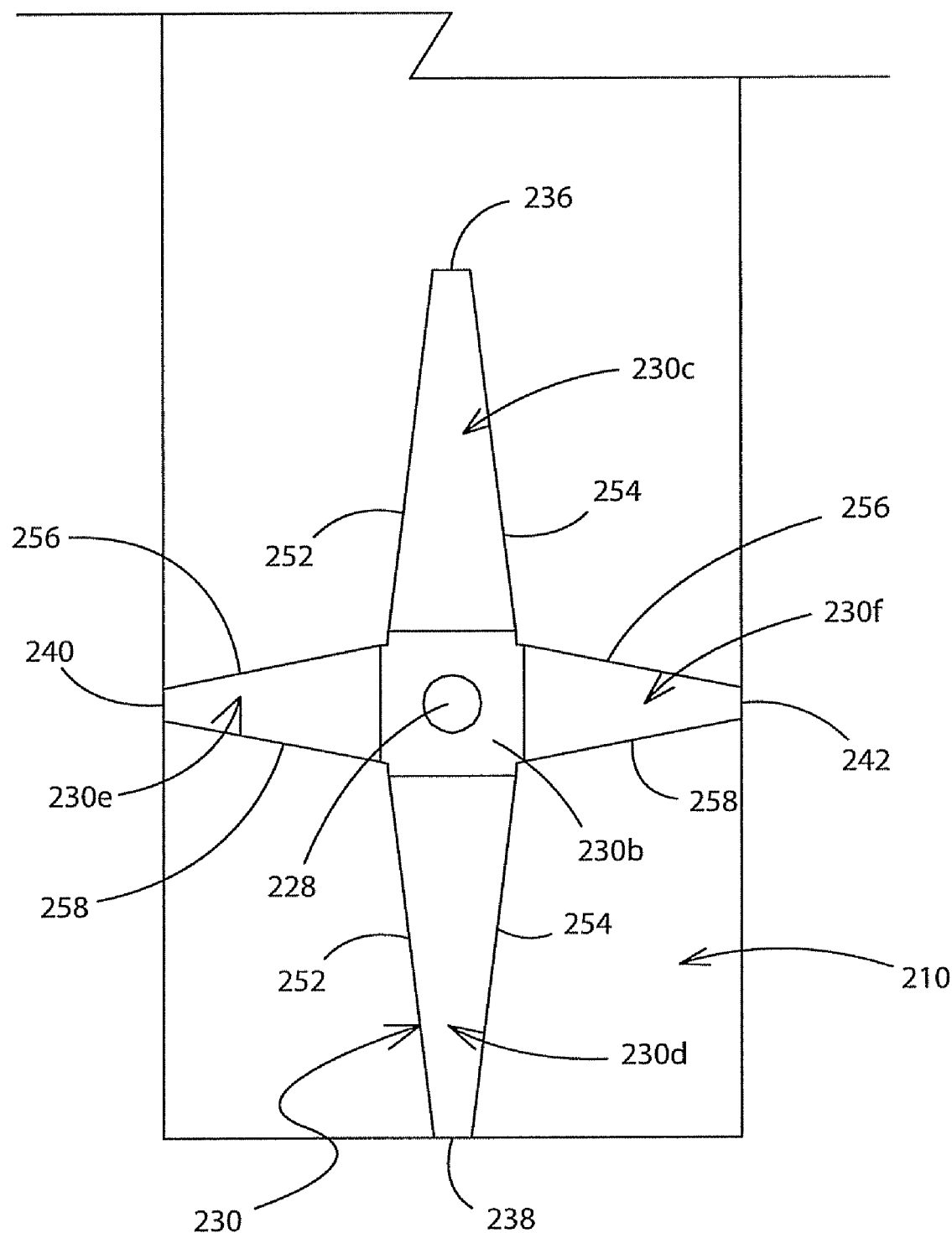
FIG. 15 is a side view of FIG. 14.

Referring to FIGS. 14 and 15 there is shown a third embodiment of a toothpick member indicated generally at 230. Toothpick member 230 extends outwardly from an interior surface 232 of a second arm 216c of a floss pick 210. Floss pick 210 may be either one of floss picks 10 and 110 or any other type of floss pick. As with the previous embodiments, a length of floss 228 extends between a first arm (not shown) of floss pick 210 and a second end 230b of toothpick member 230. FIG. 15 shows that toothpick member 230 includes first, second, third and fourth blades 230c, 230d, 230e and 230f. First and second blades 230c, 230d are substantially identical to first and second blades 130c and 130d respectively. Consequently, each of first and second blades 230c, 230d has substantially planar and straight first and second side walls 252, 254 that extend rearwardly from second end 230b to interior surface 232. Each of first and second blades 230c, 230d taper in width from where they extend outwardly from third and fourth blades 230e, 230f to their outermost walls 236, 238. First and second blades 230c, 230d also taper in height along their length from adjacent interior surface 232 to adjacent second end 230b. Thus, the height of first and second blades 230c, 230d is smaller adjacent second end 230b than adjacent interior surface 232. Finally, outermost walls 236, 238 are tapered in width, being wider adjacent second end 230b and narrower adjacent interior surface 232.

In accordance with a specific feature of this embodiment of the invention, third and fourth blades are substantially identical in shape to the first and second blades 230c, 230d and have planar and straight side walls 256, 258 and are generally a truncated-triangle in cross-sectional shape. Consequently, none of first, second, third or fourth blades 230c-230f are sinuous in nature along their lengths. Third and fourth blades 230e, 230f taper in width and height in the same way as first and second blades 230c, 203d and outermost walls 240, 242 taper in width in the same way as outermost wall 236, 238. Toothpick member 230 is used in substantially the same way as toothpick member 30.

Figure 16:
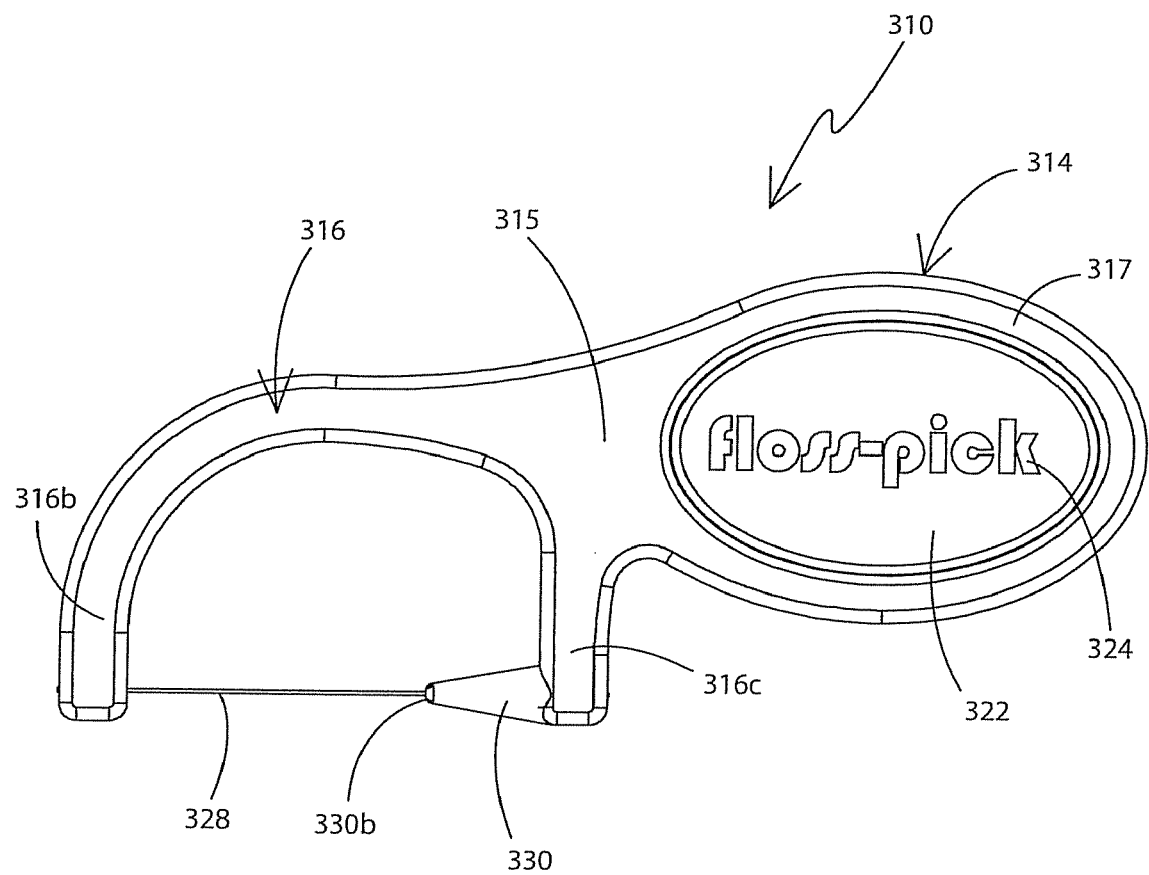
FIG. 16 is a front view of a fourth embodiment of a floss pick in accordance with the present invention showing yet another alternative handle design and an alternative toothpick or dental stimulator.
Figure 17:
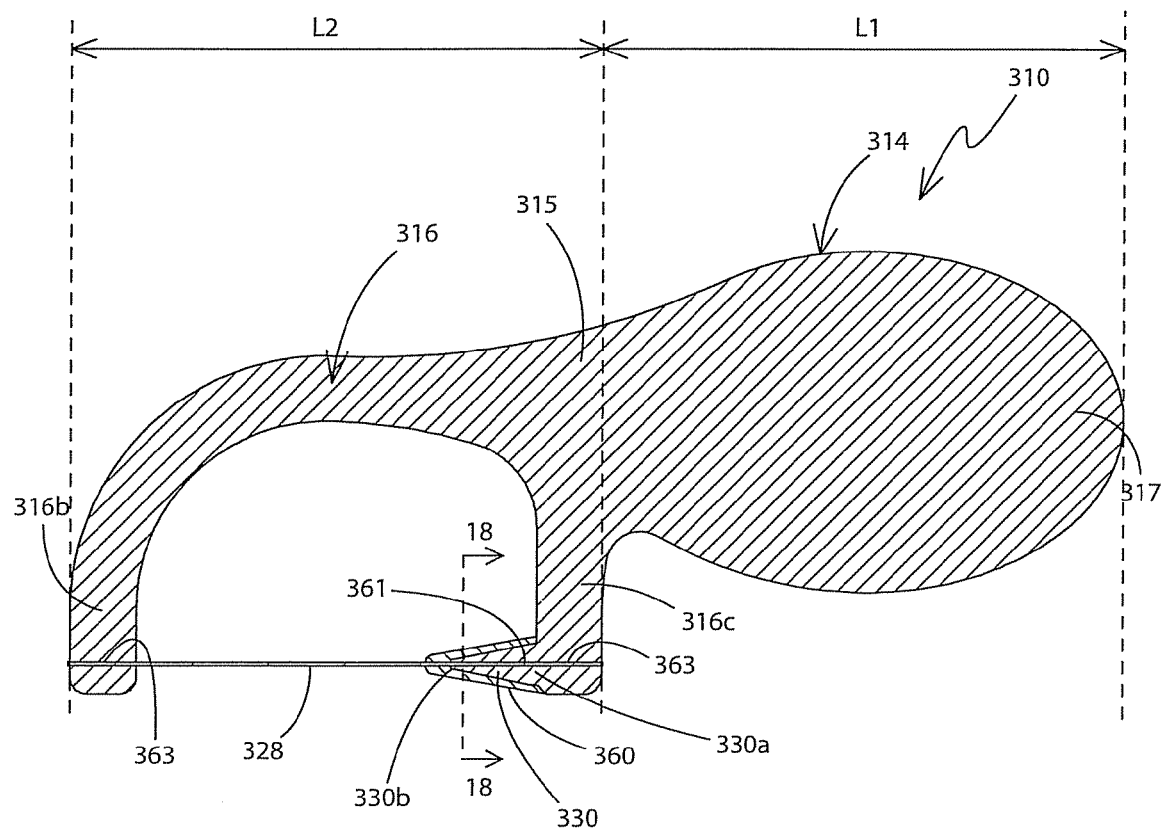
FIG. 17 is a cross-sectional view of FIG. 16.
Figure 18:
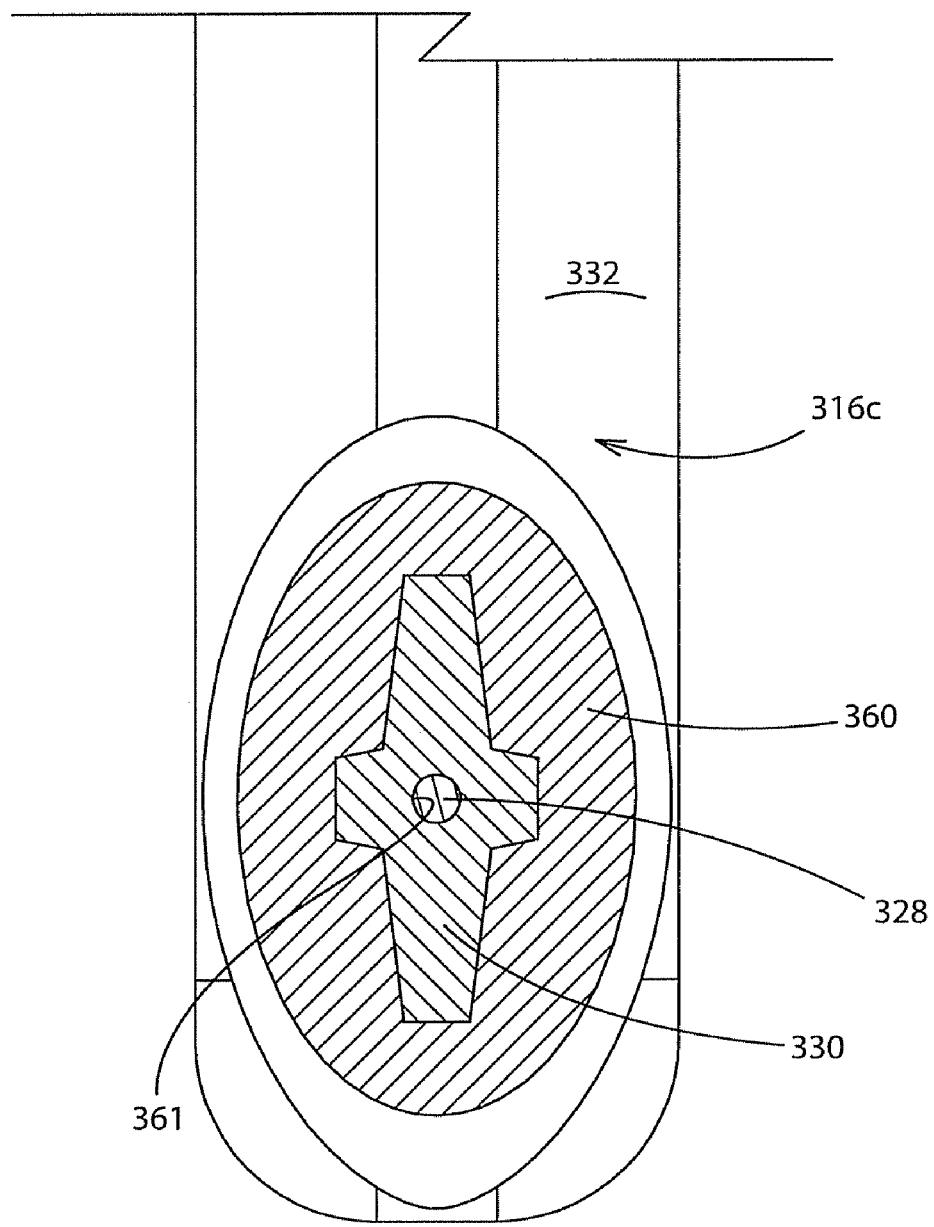
FIG. 18 is an enlarged cross-sectional side view taken through line 18-18 of FIG. 17.
Figure 19:
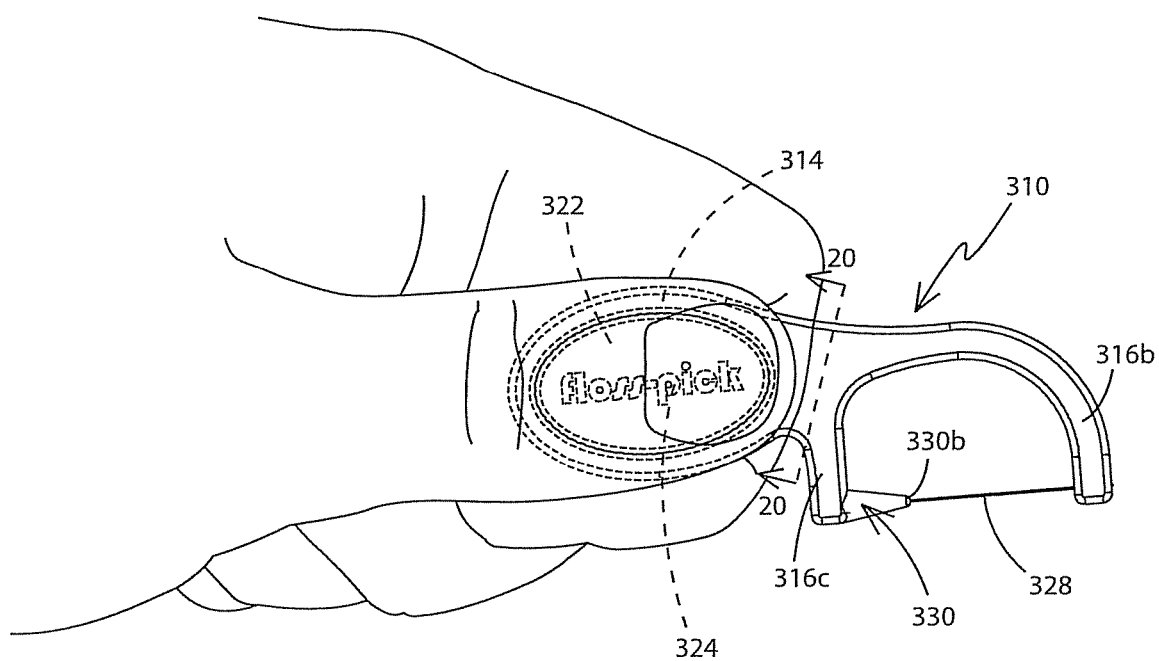
FIG. 19 is a rear view of FIG. 16 showing the floss pick held in the user's hand.
Figure 20:
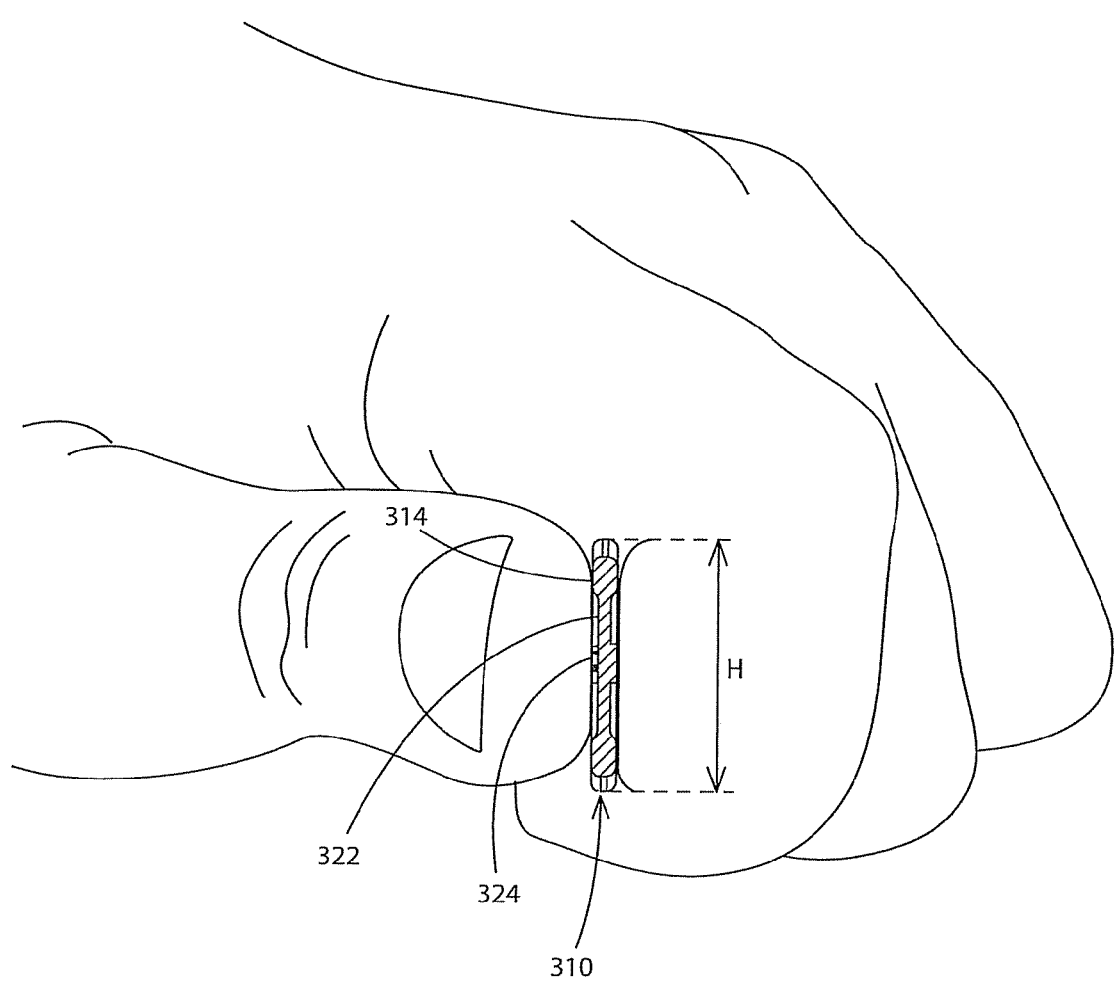
FIG. 20 is a side view of FIG. 19.
Figure 21:
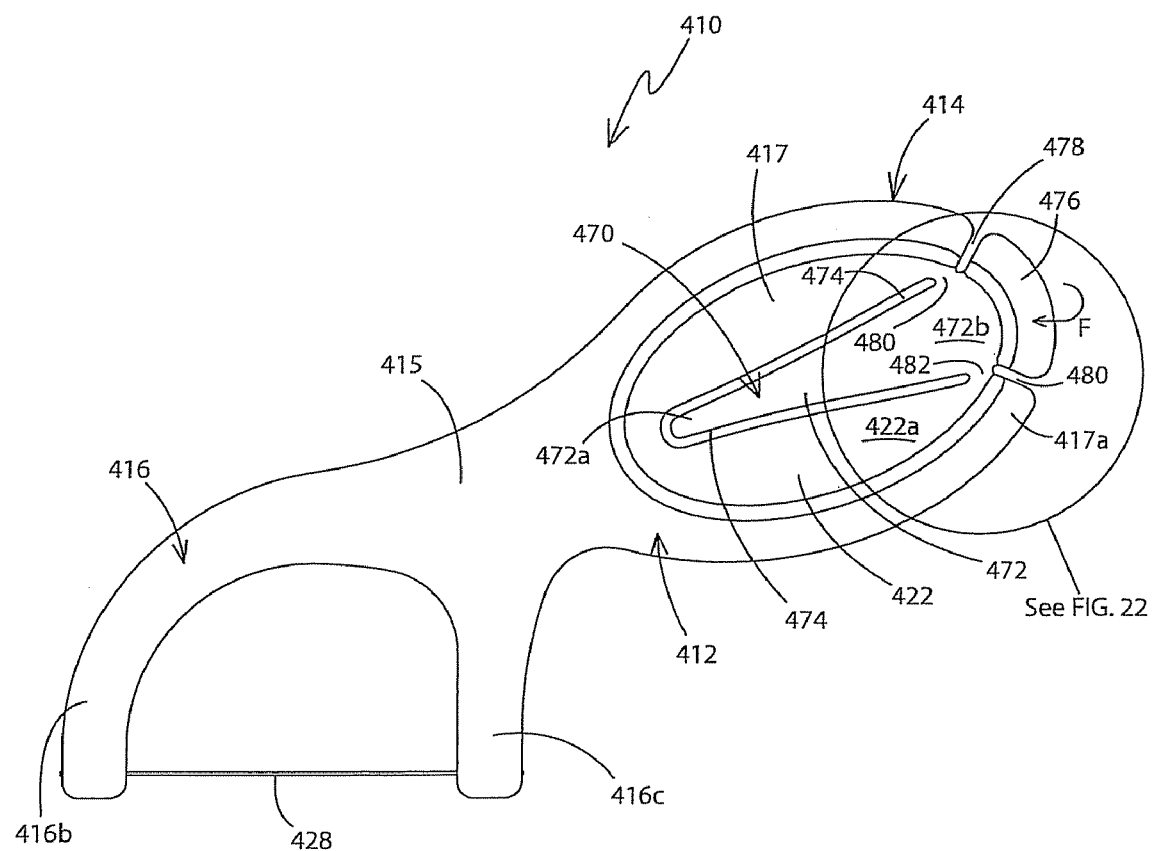
FIG. 21 is a front view of a fifth embodiment of a floss pick in accordance with the present invention.
Figure 22:
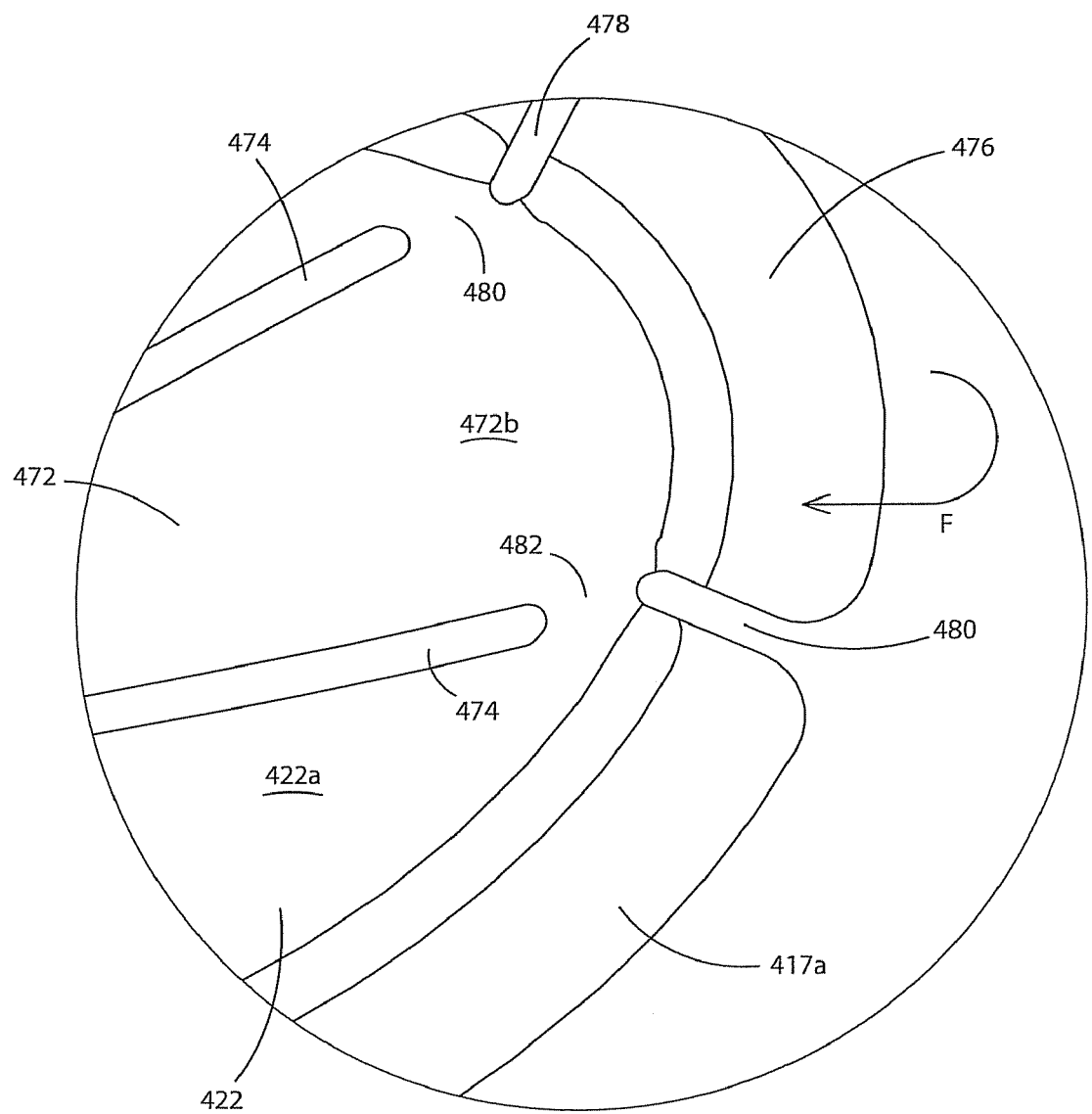
FIG. 22 is an enlarged front view of the highlighted region of FIG. 21.

Referring to FIGS. 16-18, there is shown a fourth embodiment of a floss pick in accordance with the present invention and indicated generally at 310. Floss pick 310 includes a handle 314 and head 316 and is generally F-shaped. Handle 314 comprises a neck 315 that is free of cavities and a lobe 317 that is generally oval in shape. Lobe 317 defines an oval recessed region 322 in each of the front and rear surfaces of handle 314 and recessed regions 322 may include indicia 324 therein. As with recessed regions 122 of floss pick 110, recessed regions 322 are configured to receive the pads of the user's thumb and index finger therein for easier gripping by a user. A comparison between floss pick 110 and 310 shows that lobe 317 is substantially more aligned longitudinally with head 316 than lobe 117 is with head 116. Lobe 117 and head 116 are disposed at more of an angle to each other and less in alignment with each other. The orientation of lobe 317 and head 316 has been found to be an effective configuration for both flossing and using toothpick member 330. In accordance with one of the specific features of the present invention and as shown in FIG. 17, the oval lobe 317 of handle 314 is generally equivalent in length L1 to the length L2 of head 316. Additionally, the oval shape of handle 314 and the width thereof as measured between the front and rear surfaces thereof, enable the user to more readily and easily grip floss pick 310 than was the case with previously known devices.

As with previous embodiments, toothpick member 330 is provided on head 316 and extends outwardly from second arm 316c. A length of floss 328 extends between first arm 316b and a second end 330b of toothpick member 330. Floss pick 310 is shown in cross-section in FIG. 17. As is evident from this figure, preferably all of head 316, neck 315, lobe 317 and toothpick member 330 are integrally formed, such as by injection molding. Toothpick member 330 defines an interior bore 361 that extends between the first end 330a and second end 330b thereof and generally along the longitudinal axis of toothpick member 330. Furthermore, one or both of first and second arms 316b, 316c defines a slot 363 therein. Slot 363 is in communication with bore 361 and is generally aligned therewith. At least a first portion of floss 328 is received through bore 361 and a second portion of floss 328 is received through slot 363. If slots 363 are provided in both of first and second arms 316b, 316c, then a portion of floss 328 is received in each of slots 363. Preferably, the ends of floss 328 are embedded within slots 363 of first and second arms 316b, 316c and extend through the interior bore 361 of toothpick member 330. (It should be noted that all of picks 10, 110, and 210 may be manufactured in this manner).

In accordance with a specific feature of the present invention, toothpick member 330 is provided with a sheath 360 that envelops the blades thereof. Toothpick member 330 may be configured as any one of toothpick members 30, 130 and 230. Sheath 360 preferably is made from an elastomeric material such as rubber so that it exhibits resiliency and is at the same time gentle on the user's gums. The combination of the inner X-shaped blade configuration of toothpick member 330 and the external sheath 360 make for a sturdy and functional dental stimulator. Because of the presence of sheath 360 over a portion of second end 330b, that region of toothpick member 330 is effectively rounded and floss 328 extends outwardly through an aperture in this rounded end. Floss pick 310 is used in substantially the same manner as floss pick 10. Because of the presence of shield 360 on toothpick member 330, toothpick member 330 is not only able to be used to remove plaque and debris from interproximal spaces between surfaces of adjoining teeth but is also able to massage the gum tissue surrounding at least portions of those surfaces and thereby improve the oral health of the user.

Referring to FIGS. 21-23b there is shown a fifth embodiment of a floss pick in accordance with the present invention and generally indicated at 410. Floss pick 410 includes a body 412 comprising a handle 414 and a head 416. In accordance with one of the specific features of this embodiment, handle 414 includes a preferably oval lobe 417 that is secured to head 416 by a neck 415. Lobe 417 includes a preferably oval recessed region 422 on each of the front and rear surfaces of handle 414. Recessed regions 422 are configured to receive the pads of the user's thumb and index finger so that pick 410 is more easily and securely gripped than previously known devices.

In accordance with yet another specific feature of the invention, head 416 includes a length of floss 428 therein that extends between first and second arms 416b, 416c. Unlike the previous embodiments, however, a toothpick member is not provided on the head 416 extending inwardly from one of the first and second arms 416b, 416c and secured in longitudinal alignment with floss 428. Instead, toothpick member 470 is integrally formed in handle 414. Specifically, toothpick member 470 is formed in the recessed regions 422 of lobe 417 of handle 414. Toothpick member 470 comprises a generally V-shaped region 472 that is defined by a V-shaped aperture 474 in recessed region 422. A tab 476 is defined on a portion of perimeter 417a of lobe 417 and a pair of slots 478, 480 separate tab 476 from the rest of the perimeter 417a. A bridge area 482 extends between slot 478 and aperture 474 and a second bridge area 484 extends between slot 480 and aperture 474.

It should be noted that the apex 472a of the V-shaped region 472 is disposed inwardly from the tab 476 and perimeter 417a of handle 414. Furthermore, the base region 472b of the V-shaped member 472 is disposed proximate tab 476 and perimeter 417a. V-shaped member 472 is integrally formed as part of the interior wall 422a of recessed region 422. Consequently, a front surface of V-shaped member 472 is coplanar with a front surface of interior wall 422a and a rear surface of V-shaped member 472 is coplanar with a rear surface of interior wall 422a. Additionally, it should be noted that V-shaped member 472 is positioned so that it effectively points toward head 416. Thus, when the user grasps handle 414, toothpick member 470 is shielded and will not prick or otherwise injure the user's hand.

Figure 23A:
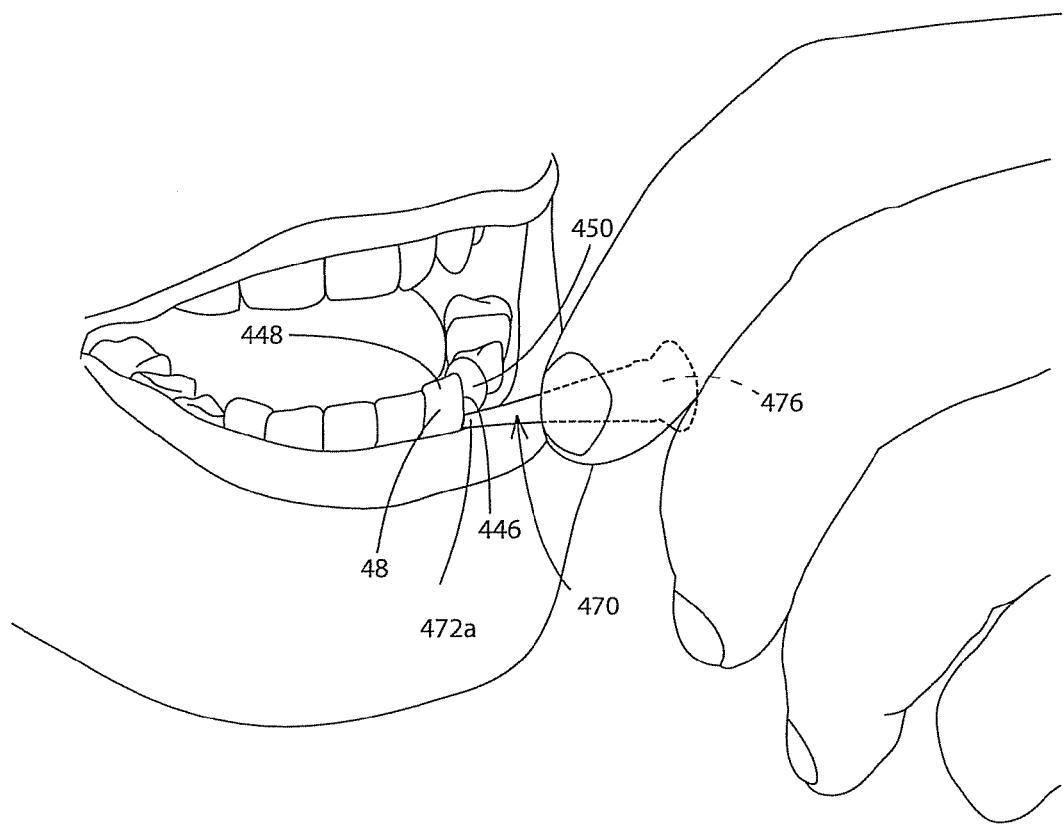
FIG. 23a is a front view of the floss pick in accordance with FIG. 21, showing the toothpick member broken away from the body of the floss pick.
Figure 23B:
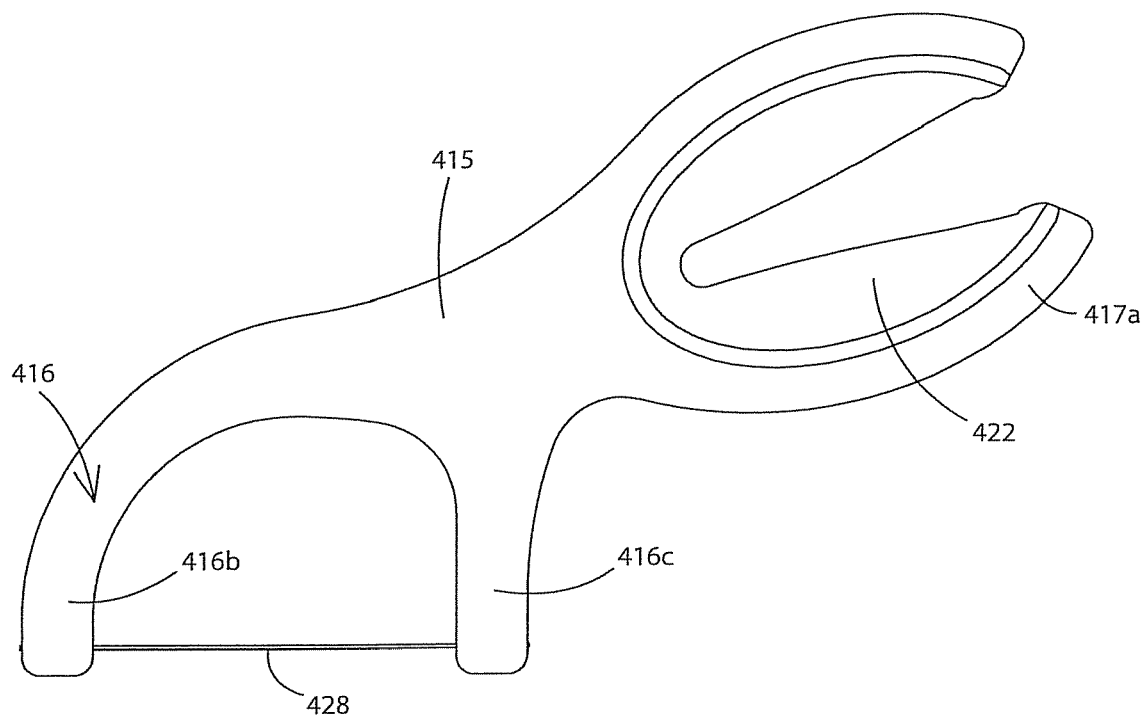
FIG. 23b is a perspective front view showing the toothpick member removed from the floss pick of FIG. 23a and being used to remove debris from an interproximal space.

Referring to FIG. 23a, 23b, floss pick 410 is used by grasping handle 414 between the thumb and index finger. As indicated previously, when the user grips floss pick 410, the pads of the thumb and index finger are seated within the recessed regions 422 on oval lobe 417. Floss pick 410 is used in the manner to floss teeth as all the previous embodiments of the floss pick. The length of floss 428 is inserted into an interproximal space 426 between two adjoining teeth 448, 450 and floss pick 410 is moved back-and-forth, up-anddown and from side-to-side to remove plaque and debris from interproximal space 446. If a particularly stubborn region of plaque or a piece of debris is lodged in interproximal space 446, the user will disengage floss 428 of floss pick 410 from space 446. Using their other hand, the user will pull tab 476 in the direction indicated by arrow "F". This movement causes the bridges 478, 480 to be torn so that slot 478 becomes continuous with one end of aperture 474 and slot 480 becomes continuous with the other end of aperture 474. When this occurs, toothpick member 470 including tab 476 becomes separated from handle 417. Toothpick member 470 may then be independently used, in the manner indicated in FIG. 23a, to remove the stubborn plaque or debris from interproximal space 446. Thus, the apex 472a of V-shaped member 472 will be inserted into interproximal space 446 and toothpick member 470 will be manipulated until the plaque or debris is dislodged. It should be noted that even though V-shaped member 472 and tab 476 have been removed therefrom, handle 414 is still easily grasped by the user to continue flossing of the teeth.

Although not specifically shown in the attached drawings, it will be understood that a toothpick member in accordance with the teachings of this description may be provided on any type of floss pick. In other words, the toothpick member could be included on floss picks that include a dispensed length of floss or where a length of floss is secured to the pick by the user. Furthermore, it should be understood that the length of floss does not have to originate in the toothpick member. Instead, the length of floss could be secured between the first and second arms of the floss pick inwardly of the free ends of those arms and the toothpick member could be provided between the length of floss and the free end of one arm.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A floss pick comprising:
a body including a handle and a head, wherein the head includes:
a first arm;
a second arm;
a cavity defined between the first arm and the second arm;
a length of dental floss extending between the first arm and the second arm and across the cavity; and
a toothpick member disposed on the head;
wherein the toothpick member has a longitudinal axis that is generally aligned with an axis of the length of floss, and the toothpick member further includes a first blade that extends radially outwardly away from the longitudinal axis of the toothpick member; and
wherein the first blade has a length that extends from the first end of the toothpick member to a second end thereof, and wherein the first blade has a height as measured from a base of the first blade to an outermost wall thereof, and wherein the height of the first blade tapers along its length from the first end of the toothpick member to the second end thereof.

2. The floss pick as defined in claim 1, wherein the first blade has a first side wall that extends between the base and the outermost wall and runs from the first end of the toothpick member to the second end thereof, and the first blade further includes a second side wall that is opposed to the first side wall, and the first blade has a width as measured between the first and the second side walls.

3. The floss pick as defined in claim 2, wherein the width of the first blade is substantially constant from proximate the base to proximate the outermost wall thereof.

4. The floss pick as defined in claim 2, wherein the width of the first blade tapers from proximate the base to proximate the outermost wall thereof.

5. The floss pick as defined in claim 1, wherein the first blade is sinuous along substantially its entire length.

6. The floss pick as defined in claim 1, wherein the first blade is planar along substantially its entire length.

7. The floss pick as defined in claim 1, wherein the toothpick member further comprises a second blade extending radially outwardly from the longitudinal axis of the toothpick member and extending from the second end of the toothpick member to adjacent the interior wall of the one of the first and the second arms of the head.

8. The floss pick as defined in claim 7, further comprising a third blade extending radially outwardly from the longitudinal axis of the toothpick member, and wherein the third blade is disposed intermediate the first and second blades, and wherein the third blade originates proximate the second end of the toothpick member and extends inwardly to proximate the interior surface of the one of the first and the second arms.

9. The floss pick as defined in claim 8, further comprising a fourth blade extending radially outwardly from the longitudinal axis of the toothpick member and disposed opposite the third blade, and wherein the fourth blade originates proximate the second end of the toothpick member and extends inwardly to proximate the interior surface of the one of the first and the second arms.

10. The floss pick as defined in claim 9, wherein each of the first, second, third and fourth blades are substantially sinuous along their lengths.

11. The floss pick as defined in claim 10, wherein the first and second blades are substantially sinuous along their lengths and the third and fourth blades are substantially planar along their lengths.

12. The floss pick as defined in claim 10, wherein each of the first, second, third and fourth blades are substantially planar along their lengths.

13. The floss pick as defined in claim 1, further comprising an elastomeric sheath disposed around an exterior surface of the toothpick member.

14. A floss pick comprising:
a body including a handle and a head, wherein the head includes:
a first arm;
a second arm;
a cavity defined between the first arm and the second arm;
a length of dental floss extending between the first arm and the second arm and across the cavity; and
a toothpick member disposed on the head;
wherein the toothpick member has a first end secured to the first arm and extends outwardly from the first arm toward the second arm to a terminal second end;
the toothpick member has a longitudinal axis that extends from the first end to the second end and is generally aligned with an axis of the length of floss, and the toothpick member further includes a first blade that extends from adjacent the first end to adjacent the second end and radially outwardly away from the longitudinal axis of the toothpick member; and wherein the first blade has first and second opposed planar surfaces which face away from one another, which extend from adjacent the first end to adjacent the second end and which extend radially outwardly away from the longitudinal axis; and wherein the first blade has a third planar surface which faces away from the longitudinal axis, which extends from adjacent the first end to adjacent the second end and which extends between the first and second planar surfaces.

15. The floss pick of claim 14 wherein the first blade has a sinuous shape.

16. A floss pick comprising:
a body including a handle and a head, wherein the head includes:
a first arm;
a second arm;
a cavity defined between the first arm and the second arm;
a length of dental floss extending between the first arm and the second arm and across the cavity; and
a toothpick member disposed on the head;
wherein the toothpick member has a first end secured to the first arm and extends outwardly from the first arm toward the second arm to a terminal second end;
the toothpick member has a longitudinal axis that extends from the first end to the second end and is generally aligned with an axis of the length of floss, and the toothpick member further includes a first blade that extends from adjacent the first end to adjacent the second end and radially outwardly away from the longitudinal axis of the toothpick member; and wherein the first blade has first and second opposed surfaces which face away from one another, which extend from adjacent the first end to adjacent the second end and which extend radially outwardly away from the longitudinal axis; and
the first blade has a third surface which faces away from the longitudinal axis, which extends from adjacent the first end to adjacent the second end, which extends between the first and second surfaces and which tapers so that the third surface is wider adjacent the second end than adjacent first end.

17. A floss pick comprising:
a body including a handle and a head, wherein the head includes:
a first arm;
a second arm;
a cavity defined between the first arm and the second arm;
a length of dental floss extending between the first arm and the second arm and across the cavity; and
a toothpick member disposed on the head;
wherein the toothpick member has a first end secured to the first arm and extends outwardly from the first arm toward the second arm to a terminal second end;
the toothpick member has a longitudinal axis that extends from the first end to the second end and is generally aligned with an axis of the length of floss, and the toothpick member further includes a first blade that extends from adjacent the first end to adjacent the second end and radially outwardly away from the longitudinal axis of the toothpick member: and wherein the first blade extends radially outwardly away from the longitudinal axis in a first direction;
the toothpick member includes a second blade that extends from adjacent the first end to adjacent the second end and radially outwardly away from the longitudinal axis in a second direction different than the first direction.

18. The floss pick of claim 17 wherein the first direction is upward away from the longitudinal axis; and
the second direction is one of forward and rearward away from the longitudinal axis.

19. The floss pick of claim 17 wherein the first direction is upward away from the longitudinal axis; and
the second direction is downward away from the longitudinal axis.

20. The floss pick of claim 17 wherein the first blade is disposed generally at ninety degrees relative to the second blade.

21. The floss pick of claim 17 wherein the first blade is disposed substantially at 180 degrees relative to the second blade.

22. The floss pick of claim 17 wherein the first and second blades are substantially identical in shape.

23. The floss pick of claim 17 wherein the first and second blades are different in shape.

* * * * *